(12) United States Patent
Cullis et al.

(10) Patent No.: US 12,233,416 B2
(45) Date of Patent: *Feb. 25, 2025

(54) LIMIT SIZE LIPID NANOPARTICLES AND RELATED METHODS

(71) Applicant: The University of British Columbia, Vancouver (CA)

(72) Inventors: Pieter R. Cullis, Vancouver (CA); Igor V. Jigaltsev, Vancouver (CA); Robert James Taylor, Vancouver (CA); Timothy Leaver, Delta (CA); Andre Wild, Vancouver (CA); Nathan Maurice Belliveau, Weymouth (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/296,954

(22) Filed: Apr. 6, 2023

(65) Prior Publication Data

US 2023/0256436 A1 Aug. 17, 2023

Related U.S. Application Data

(63) Continuation of application No. 17/061,247, filed on Oct. 1, 2020, now Pat. No. 11,648,556, which is a continuation of application No. 15/927,925, filed on Mar. 21, 2018, now Pat. No. 10,843,194, which is a continuation of application No. 15/087,721, filed on Mar. 31, 2016, now Pat. No. 9,943,846, which is a continuation of application No. 14/353,460, filed as application No. PCT/CA2012/000991 on Oct. 25, 2012, now abandoned.

(60) Provisional application No. 61/551,366, filed on Oct. 25, 2011.

(51) Int. Cl.

| | |
|---|---|
| A61K 9/16 | (2006.01) |
| A61J 3/00 | (2006.01) |
| A61K 9/107 | (2006.01) |
| A61K 9/127 | (2006.01) |
| A61K 9/1271 | (2025.01) |
| A61K 9/1277 | (2025.01) |
| A61K 9/14 | (2006.01) |
| A61K 31/704 | (2006.01) |
| A61K 47/44 | (2017.01) |
| A61K 49/00 | (2006.01) |
| B01F 23/41 | (2022.01) |
| B01F 25/431 | (2022.01) |
| B01F 25/433 | (2022.01) |
| B01F 33/30 | (2022.01) |
| B01L 3/00 | (2006.01) |

(52) U.S. Cl.
CPC ............ *B01L 3/50273* (2013.01); *A61J 3/00* (2013.01); *A61K 9/1075* (2013.01); *A61K 9/127* (2013.01); *A61K 9/1271* (2013.01); *A61K 9/1277* (2013.01); *A61K 9/14* (2013.01); *A61K 31/704* (2013.01); *A61K 47/44* (2013.01); *A61K 49/0002* (2013.01); *B01F 23/41* (2022.01); *B01F 25/4317* (2022.01); *B01F 25/4331* (2022.01); *B01F 33/30* (2022.01); *B01L 3/502715* (2013.01); *B01F 25/431971* (2022.01); *B01L 2200/0605* (2013.01); *B01L 2200/0647* (2013.01); *B01L 2300/06* (2013.01); *B01L 2300/0848* (2013.01); *B01L 2300/0867* (2013.01); *B01L 2300/18* (2013.01); *Y10T 428/2982* (2015.01)

(58) Field of Classification Search
CPC ... A61K 9/1688; A61K 9/1682; A61K 9/1694
See application file for complete search history.

(56) References Cited

U.S. PATENT DOCUMENTS

| | | |
|---|---|---|
| 5,921,678 A | 7/1999 | Desai |
| 5,981,501 A | 11/1999 | Wheeler |
| 6,479,299 B1 | 11/2002 | Parce |
| 6,815,432 B2 | 11/2004 | Wheeler |
| 6,843,942 B2 | 1/2005 | Katinger |
| 7,005,140 B2 | 2/2006 | Zhang |
| 7,160,025 B2 | 1/2007 | Ji |
| 7,214,348 B2 | 5/2007 | Desmond |
| 7,252,928 B1 | 8/2007 | Hafeman |
| 7,507,380 B2 | 3/2009 | Chang |
| 7,622,509 B2 | 11/2009 | Tonkovich |
| 7,708,949 B2 | 5/2010 | Stone |
| 7,745,221 B2 | 6/2010 | Butler |
| 7,794,136 B2 | 9/2010 | Yang |
| 7,901,708 B2 | 3/2011 | MacLachlan |
| 8,058,069 B2 | 11/2011 | Yaworski |

(Continued)

FOREIGN PATENT DOCUMENTS

| | | |
|---|---|---|
| CA | 2427640 A1 | 5/2003 |
| CA | 2491164 A1 | 1/2004 |

(Continued)

OTHER PUBLICATIONS

First-Final Office Action mailed Jan. 7, 2020, issued in Japanese Patent Application No. 2019-022341, filed Oct. 25, 2012, 4 pages.
Kitazoe, K. et al. "A Microdevice With Chaotic Mixer to Constract Multofunctional Envelope-Type Nanodevice for Delivery System," 14th International Conference on Miniaturized Systems for Chemistry and Life Sciences, Oct. 3-7, 2010, Groningen, The Netherlands, pp. 827-829.
Jahn, A. et al., "Microfluidic Mixing and the Formation of Nanoscale Lipid Vesicles," ACS Nano, 4:4; Apr. 27, 2010, pp. 2077-2087.

(Continued)

*Primary Examiner* — Micah Paul Young
(74) *Attorney, Agent, or Firm* — Christensen O'Connor Johnson Kindness PLLC

(57) ABSTRACT

Limit size lipid nanoparticles, methods for using the lipid nanoparticles, and methods and systems for making limit size lipid nanoparticles.

19 Claims, 21 Drawing Sheets

(56) References Cited

U.S. PATENT DOCUMENTS

| | | | |
|---|---|---|---|
| 8,106,176 | B2 | 1/2012 | Aurisicchio |
| 8,122,909 | B2 | 2/2012 | Tonkovich |
| 8,137,699 | B2 | 3/2012 | Johnson |
| 8,273,573 | B2 | 9/2012 | Ismagilov |
| 8,329,070 | B2 | 12/2012 | Maclachlan |
| 8,361,415 | B2 | 1/2013 | Di Carlo |
| 8,367,004 | B2 | 2/2013 | Panagiotou |
| 8,414,182 | B2 | 4/2013 | Paul |
| 8,492,359 | B2 | 7/2013 | Yaworski |
| 8,496,961 | B2 | 7/2013 | Hong |
| 8,522,413 | B2 | 9/2013 | Van'T Oever |
| 8,883,200 | B2 | 11/2014 | Hong |
| 9,005,654 | B2 | 4/2015 | Maclachlan |
| 9,943,846 | B2 * | 4/2018 | Cullis ................. B01F 25/4331 |
| 10,843,194 | B2 * | 11/2020 | Cullis ................. A61K 9/1277 |
| 11,648,556 | B2 * | 5/2023 | Cullis ............... B01L 3/502715 |
| | | | 422/505 |
| 2004/0262223 | A1 | 12/2004 | Strook |
| 2006/0108012 | A1 | 5/2006 | Barrow |
| 2006/0219307 | A1 | 10/2006 | Wang |
| 2007/0263485 | A1 | 11/2007 | Yang |
| 2010/0022680 | A1 * | 1/2010 | Karnik ................. B01F 25/314 |
| | | | 523/105 |
| 2011/0070292 | A1 | 3/2011 | Javeri |
| 2011/0182994 | A1 | 7/2011 | Kornfield |
| 2011/0305734 | A1 | 12/2011 | Edelson |
| 2012/0276209 | A1 | 11/2012 | Cullis |
| 2013/0303587 | A1 | 11/2013 | Yaworski |

FOREIGN PATENT DOCUMENTS

| | | |
|---|---|---|
| CA | 2578574 A1 | 2/2006 |
| CA | 2579695 A1 | 3/2006 |
| CA | 2616877 A1 | 2/2007 |
| CA | 2673924 A1 | 7/2008 |
| CA | 2781527 A1 | 3/2011 |
| EP | 2123260 A1 | 11/2009 |
| JP | 2005-525815 A | 9/2005 |
| JP | 2006-082073 A | 3/2006 |
| JP | 2007-513122 A | 5/2007 |
| JP | 2007-524604 A | 8/2007 |
| JP | 2007-533647 A | 11/2007 |
| JP | 2009-509553 A | 3/2009 |
| JP | 2010-514708 A | 5/2010 |
| JP | 2010-180353 A | 8/2010 |
| WO | 03/097805 A2 | 11/2003 |
| WO | 2005/039535 A1 | 5/2005 |
| WO | 2005/053642 A1 | 6/2005 |
| WO | 2005/120152 A2 | 12/2005 |
| WO | 2005/120461 A2 | 12/2005 |
| WO | 2007/150030 A2 | 12/2007 |
| WO | 2008/053988 A1 | 5/2008 |
| WO | 2009/086558 A1 | 7/2009 |
| WO | 2009/127060 A1 | 10/2009 |
| WO | 2010/055106 A1 | 5/2010 |
| WO | 2012/000104 A1 | 1/2012 |
| WO | 2012/016184 A2 | 2/2012 |

OTHER PUBLICATIONS

Wheeler, J. J. et al., "Polyethylene Glycol Modified Phospholipids Stabilize Emulsions Prepared from Triacylglycerol," Journal of Pharmaceutical Sciences, American Chemical Society and American Pharmaceutical Association, US, 83:11; Nov. 1, 1994, pp. 1558-15464.
Extended European Search Report mailed on Sep. 28, 2021. issued in corresponding European Application No. 21169020.1, filed on Jun. 22, 2021, 13 pages.
Abrams, M.T., et al., "Evaluation of Efficacy, Biodistribution, and Inflammation for a Potent siRNA Nanoparticle: Effect of Dexamethasone Co-Treatment," Molecular Therapy 18(1):171-180, Jan. 2010.
Avnir, Y., et al., Amphipathic Weak Acid Glucocorticoid Prodrugs Remote-Loaded Into Sterically Stabilized Nanoliposomes Evaluated in Arthritic Rats and in a Beagle Dog: A Novel Approach to Treating Autoimmune Arthritis, Arthritis & Rheumatism 58(1):119-129, Jan. 2008.
Belliveau, N.M., et al., "Microfluidic Synthesis of Highly Potent Limit-Size Lipid Nanoparticles for In Vivo Delivery of siRNA," Molecular Therapy-Nucleic Acids 1(8):e37, Aug. 2012, 9 pages.
Chen, D., et al., "Rapid Discovery of Potent siRNA-Containing lipid Nanoparticles Enabled by Controlled Microfluidic Formulation," Journal of the American Chemical Society 134( 16):6948-6951, Apr. 2012.
Crawford, R., et al., "Analysis of Lipid Nanoparticles by Cryo-EM for Characterizing siRNA Delivery Vehicles," International Journal of Pharmaceutics 403(1-2):237-244, Jan. 2011.
Deamer, D.W., and P.S. Uster, "Liposome Preparation: Methods and Mechanisms," in M.J. Ostra (ed.), "Liposomes," Marcel Dekker, New York, 1983, pp. 27-52.
Geusens, B., et al., "Ultradeformable Cationic Liposomes for Delivery of Small Interfering RNA {siRNA) Into Human Primary Melanocytes," Journal of Controlled Release 133(3):214-220, Feb. 2009.
Gindy, M.E., et al., "Mechanism of Macromolecular Structure Evolution in Self-Assembled Lipid Nanoparticles for siRNA Delivery," Langmuir 30(16):4613-4622, Apr. 2014.
Heyes, J., et al., "Lipid Encapsulation Enables the Effective Systemic Delivery of Polyplex Plasmid DNA," Molecular Therapy 15(4):713-720, Apr. 2007.
Hope, M.J., et al., "Generation of Multilamellar and Unilamellar Phospholipid Vesicles," Chemistry and Physics of Lipids 40(2-4 ):89-107, Jun.-Jul. 1986.
Jahn, A., et al., "Preparation of Nanoparticles by Continuous-Flow Microfluidics," Journal of Nanoparticle Research 10(6):925-934, Aug. 2008.
Jeffs, L.B., et al., "A Scalable, Extrusion-Free Method for Efficient Liposomal Encapsulation of Plasmid DNA," Pharmaceutical Research 22(3):362-372, Mar. 2005.
Johnson, B.K., and R.K. Prud'Homme, "Mechanism for Rapid Self-Assembly of Block Copolymer Nanoparticles," Physical Review Letters 91(11):118302-1-118302-4, Sep. 2003.
Kapoor, M., et al., "Physicochemical Characterization Techniques for Lipid Based Delivery Systems for siRNA," International Journal of Pharmaceutics 427(1 ):35-57, May 2012.
Karnik, R., et al., "Microfluidic Platform for Controlled Synthesis of Polymeric Nanoparticles," Nano Letters 8(9):2906-2912, Sep. 2008.
Koh, C.G., et al., "Delivery of Antisense Oligodeoxyribonucleotide Lipopolyplex Nanoparticles Assembled by Microfiuidic Hydrodynamic Focusing," Journal of Controlled Release 141(1):62-69, Jan. 2010.
MacLachlan, I., "Liposomal Formulations for Nucleic Acid Delivery," in S.T. Crooke (ed.), "Antisense Drug Technology: Principles, Strategies, and Applications," 2nd ed., Chap. 9, CRC Press, Jul. 2007.
Montana, G., et al., "Employment of Cationic Solid-Lipid Nanoparticles as RNA Carriers," Bioconjugate Chemistry 18:302-308, Published on Web Jan. 25, 2007.
Peer, D., and R. Margalit, "Tumor-Targeted Hyaluronan Nanoliposomes Increase the Antitumor Activity of Liposomal Doxorubicin in Syngeneic and Human Xenografl Mouse Tumor Models," Neoplasia 6(4):343-353, Jul.-Aug. 2004.
Rudra, A., et al., "Doxorubicin-Loaded Phosphatidylelhanolamine-Conjugated Nanoliposomes: In Vitro Characterization and Their Accumulation in Liver, Kidneys, and Lungs in Rats," International Journal of Nanomedicine 5:811-823, Oct. 2010.
Seo, M., et al., "Microfluidic Assembly of Monodisperse, Nanoparticle-Incorporated Perfluorocarbon Microbubbles for Medical Imaging and Therapy," Langmuir 26(17):13855-13860, Published on Web Jul. 28, 2010.
Szoka, F., Jr., "Comparative Properties and Methods of Preparation of Lipid Vesicles (Liposomes)," Annual Review of Biophysics and Bioengineering 9:467-508, 1980.
Vemuri, S., and C.T. Rhodes, "Preparation and Characterization of Liposomes as Therapeutic Delivery Systems: A Review," Pharmaceutica Acta Helvetiae 70(2):95-111, Jul. 1995.

(56) References Cited

OTHER PUBLICATIONS

Ku, Y., et al., "Physicochemical Characterization and Purification of Cationic Lipoplexes," Biophysical Journal 77(1):341-353, Jul. 1999.
Yu, B., et al., "Microfluidic Methods for Production of Liposomes," Methods in Enzymology 465:129-141, 2009.
Zhang, J., et al., "Assessing the Heterogeneity Level in Lipid Nanoparticles for siRNA Delivery: Size-Based Separation, Composition at Heterogeneity, and Impact of Bioperformance," Molecular Pharmaceutics 10(1):397-405, Jan. 2013.
Zhang, J., et al., "Polydispersity Characterization of Lipid Nanoparticles for siRNA Delivery Using Multiple Detection Size-Exclusion Chromatography," Analytical Chemistry 84(14):6088-6096, Jul. 2012.
Zhigal Tsev, IV., et al., "Bottom-Up Design and Synthesis of Limit Size Lipid Nanoparticle Systems With Aqueous and Triglyceride Cores Using Millisecond Microfluidic Mixing," Langmuir 28(7):3633-3640, Feb. 2012.
First Office Action mailed Jul. 15, 2014, issued in Japanese Patent Application No. 2012-537274, filed Nov. 4, 2010, 5 pages.
Decision of Rejection mailed Apr. 7, 2015 (with foreign associate's comments), issued in Japanese Application No. 2012-537274, filed Nov. 4, 2010, 6 pages.
International Search Report and Written Opinion mailed Feb. 8, 2011, issued in International Application No. PCT/CA2010/001766, filed Nov. 4, 2010, 17 pages.
International Preliminary Report on Patentability mailed May 18, 2012, issued in International Application No. PCT/CA2010/001766, filed Nov. 4, 2010, 11 pages.
Notification Concerning Transmittal of International Preliminary Report on Patentability, International Preliminary Report on Patentability and Written Opinion mailed May 18, 2012, issued in International Application No. PCT/CA2010/001766, filed Nov. 4, 2010, 11 pages.
International Search Report mailed Feb. 18, 2013, issued in International Application No. PCT/CA2012/000991, filed Oct. 25, 2012, 18 pages.
Notification of the Second Office Action, issued Jan. 24, 2014, in Chinese Application No. 201080059999.7, filed Nov. 4, 2010, 7 pages.
Notification of the Third Office Action, mailed Oct. 15, 2014, issued in Chinese Application No. 201080059999.7, filed Nov. 4, 2010, 7 pages.
Notification of the Fourth Office Action mailed Jul. 6, 2015, issued in Chinese Application No. 201080059999.7, filed Nov. 4, 2010, 10 pages.
Office Action mailed Oct. 10, 2014, issued in Russian Application No. 2012122776, filed Nov. 4, 2010, 12 pages.
Partial Supplementary European Search Report mailed Jun. 1, 2015, issued in corresponding European Application No. 12843980.9, filed Oct. 25, 2012, 5 pages.
Extended European Search Report mailed Oct. 6, 2015, issued in corresponding European Application No. 12843980.9, filed Oct. 25, 2012, 7 pages.
Supplementary European Search Report mailed Dec. 6, 2013, issued in European Application No. 10 85 1175.9, filed Nov. 4, 2010, 10 pages.
Communication Pursuant to Article 94(3) EPC, issued Jul. 18, 2014, in European Application No. 10 85 1175.9, filed Nov. 4, 2010, 7 pages.
Extended European Search Report mailed Jul. 8, 2016, issued in corresponding European Patent Application No. 16166730.8, filed Oct. 25, 2012, 6 pages.
First Office Action mailed Jul. 20, 2016, issued in corresponding Japanese Application No. 2014-537433, filed Oct. 25, 2012, 8 pages.
Examination Search Report mailed Aug. 29, 2017, issued in corresponding Canadian Application No. 2,853,316, filed Oct. 25, 2012, 5 pages.
First Japanese Office Action mailed Feb. 9, 2018, issued in corresponding Japanese Application No. 2016-245508, filed Oct. 25, 2012, 3 pages.

* cited by examiner

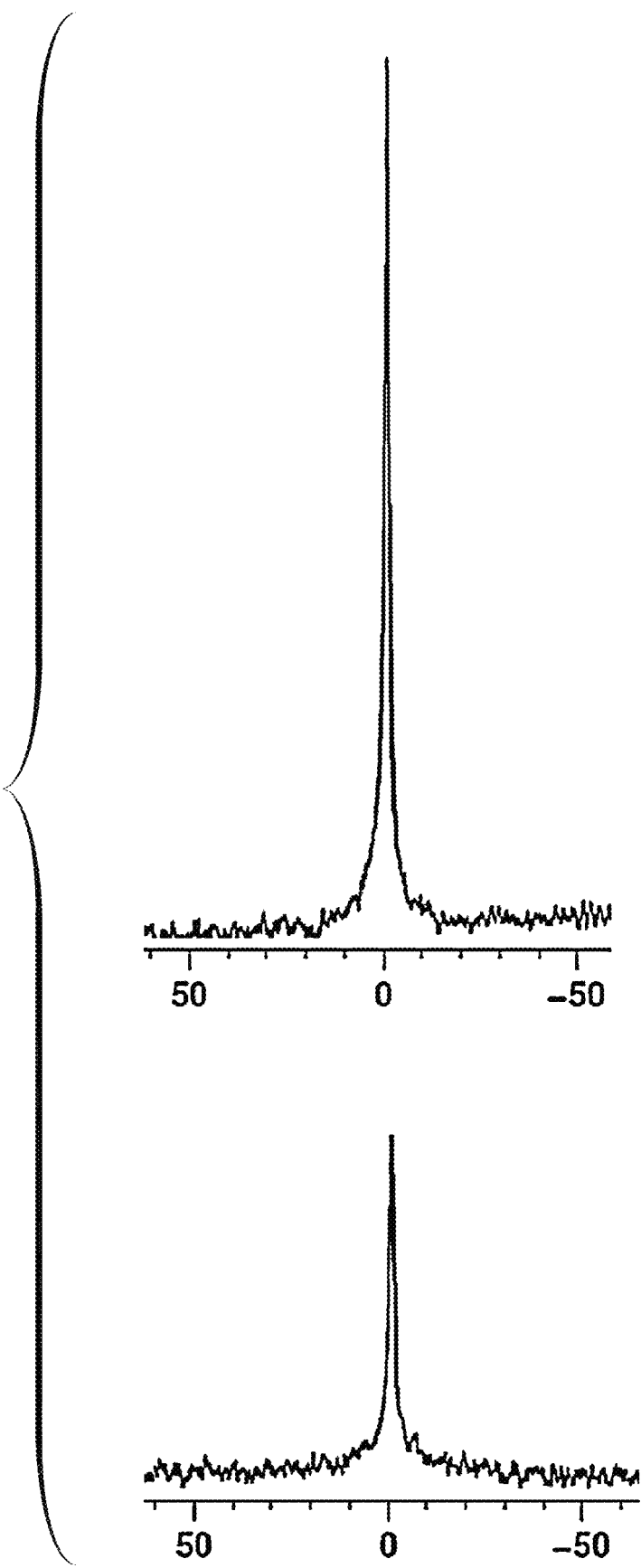

LIMIT SIZE LIPID NANOPARTICLES AND RELATED METHODS

CROSS-REFERENCES TO RELATED APPLICATIONS

This application is a continuation of U.S. patent application Ser. No. 17/061,247, filed Oct. 1, 2020, which is a continuation of U.S. patent application Ser. No. 15/927,925, filed Mar. 21, 2018, now patent Ser. No. 10/843,194, which is a continuation of U.S. patent application Ser. No. 15/087,721, filed Mar. 31, 2016, now U.S. Pat. No. 9,943,846, which is a continuation of U.S. patent application Ser. No. 14/353,460, filed Apr. 22, 2014, which is a National Stage of PCT/CA2012/000991, filed Oct. 25, 2012, which claims the benefit of U.S. Patent Application No. 61/551,366, filed Oct. 25, 2011, all of which are expressly incorporated herein by reference in their entirety.

FIELD OF THE INVENTION

The present invention is directed to limit size nanoparticles for delivery of therapeutic and/or diagnostic agents, methods for using the lipid nanoparticles, and methods and systems for making the lipid nanoparticles.

BACKGROUND

The ability to produce the smallest particles possible (the "limit size") from lipid components is important for applications ranging from drug delivery to the production of cosmetics. In the area of drug delivery, for example, size is an important determinant of the biodistribution of lipid nanoparticles (LNP) following intravenous (i.v.) injection. Long-circulating LNP of diameter 100 nm or smaller are able to preferentially accumulate at disease sites such as tumors and sites of infection and inflammation due to their ability to extravasate through the leaky vasculature in such regions. LNP smaller than approximately 50 nm diameter can permeate through the lymphatics and accumulate in tissues such as bone marrow whereas particles of 30 nm or smaller can access progressively more tissues in the body. Particles smaller than approximately 8 nm diameter are cleared by the kidney. It is therefore particularly important to be able to generate particles in the size range 10-50 nm as these particles are most likely to be able to access extravascular target tissue.

Methods of making limit size LNP have not progressed substantially for nearly 30 years. All of the methods employ "top down" approaches where larger structures are formed by dispersion of lipid in water, followed by mechanical disruption to produce smaller systems. The preferred method for making bilayer vesicles in the 100 nm size range involves extrusion of preformed multilamellar vesicles (micron size range) through polycarbonate filters with a pore size of 100 nm or smaller and is not useful for producing systems smaller than approximately 50 nm. The predominant method for making limit size systems has usually involved sonication of multilamellar vesicles, usually tip sonication, which has limitations of sample contamination, sample degradation and, most importantly, lack of scalability. For lipid systems containing bilayer-forming lipids such as phosphatidylcholine (PC), sonication results in limit size vesicular LNP as small as 20 nm diameter, whereas PC/cholesterol (Chol) systems result in somewhat larger LNP. Alternatively, for production of nanoemulsions consisting of PC and non-polar lipids such as triglycerides, sonication or other emulsification techniques have been applied. However the production of stable systems with size ranges less than 50 nm has proven elusive.

Although LNPs of useful size can be prepared by conventional top down methods, a need exists for improved methods that facilitate the scalable preparation of these LNPs. The present seeks to fulfill this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides limit size lipid nanoparticles useful for delivery of therapeutic and/or diagnostic agents. In one embodiment, the limit size lipid nanoparticle has a diameter from about 10 to about 100 nm. In certain embodiments, the lipid nanoparticle has a lipid bilayer surrounding an aqueous core. The lipid bilayer includes a phospholipid. In other embodiments, the lipid nanoparticle has a lipid monolayer surrounding a hydrophobic core. The lipid monolayer includes a phospholipid. In certain embodiments, the nanoparticle includes a lipid bilayer surrounding an aqueous core, wherein the bilayer includes a phospholipid, a sterol, and a polyethylene glycol-lipid, and the core comprises a therapeutic or diagnostic agent. In other embodiments, the nanoparticle includes a lipid monolayer surrounding a hydrophobic core, wherein the monolayer comprises a phospholipid, and the core comprises a fatty acid triglyceride and a therapeutic and/or diagnostic agent.

In other aspects, methods of using the nanoparticles are provided. In one embodiment, the invention provides a method for administering a therapeutic agent to a subject, comprising administering a nanoparticle of the invention to a subject in need thereof. In another embodiment, the invention provides a method for administering a diagnostic agent to a subject, comprising administering a nanoparticle of the invention to a subject in need thereof. In a further embodiment, the invention provides a method for treating a disease or condition treatable by administering a therapeutic agent, comprising administering a therapeutically effective amount of a nanoparticle of the invention to a subject in need thereof. In another embodiment, the invention provides a method for diagnosing a disease or condition diagnosable by administering a diagnostic agent, comprising administering a nanoparticle of the invention to a subject in need thereof.

In a further aspect of the invention, methods for making limit size nanoparticles are provided. In one embodiment, the method includes making limit size lipid nanoparticles in a device having a first region adapted for flow of first and second adjacent streams and a second region for mixing the streams, comprising:

(a) introducing a first stream comprising a first solvent into the device at a first flow rate;

(b) introducing a second stream comprising lipid particle-forming materials in a second solvent into the device at a second flow rate to provide first and second adjacent streams, wherein the first and second solvents are not the same, and wherein the ratio of the first flow rate to the second flow rate is from about 2.0 to about 10.0;

(c) flowing the first and second streams from the first region to the second region; and (d) mixing the first and second streams in the second region of the device to provide a third stream comprising lipid nanoparticles.

In another aspect, the invention provides devices for making limit size lipid nanoparticles.

In one embodiment, the device includes:

(a) a first inlet for receiving a first solution comprising a first solvent;

(b) a first inlet microchannel in fluid communication with the first inlet to provide a first stream comprising the first solvent;

(c) a second inlet for receiving a second solution comprising lipid particle-forming materials in a second solvent;

(d) a second inlet microchannel in fluid communication with the second inlet to provide a second stream comprising the lipid particle-forming materials in the second solvent; and (e) a third microchannel for receiving the first and second streams, wherein the third microchannel has a first region adapted for flowing the first and second streams and a second region adapted for mixing the contents of the first and second streams to provide a third stream comprising limit size lipid nanoparticles.

In another embodiment, the device includes:

(a) a first inlet for receiving a first solution comprising a first solvent;

(b) a first inlet microchannel in fluid communication with the first inlet to provide a first stream comprising the first solvent;

(c) a second inlet for receiving a second solution comprising lipid particle-forming materials in a second solvent;

(d) a second inlet microchannel in fluid communication with the second inlet to provide a second stream comprising the lipid particle-forming materials in the second solvent;

(e) a plurality of microchannels for receiving the first and second streams, wherein each has a first region adapted for flowing the first and second streams and a second region adapted for mixing the contents of the first and second streams to provide a plurality of streams compromising lipid nanoparticles; and (f) a fourth microchannel for receiving and combining the plurality of streams comprising lipid nanoparticle. In this embodiment, each of the plurality of microchannels for receiving the first and second streams may include:

(a) a first microchannel in fluidic communication with the first inlet microchannel to receive the first stream comprising the first solvent;

(b) a second microchannel in fluidic communication with the second inlet microchannel to receive the second inlet stream comprising the second solvent; and (c) a third microchannel for receiving the first and second streams, wherein each has a first region adapted for flowing the first and second streams and a second region adapted for mixing the contents of the first and second streams to provide a plurality of streams compromising lipid nanoparticles.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 3A-3C present $^{31}$P-NMR spectra of POPC (FIG. 3A); POPC/Chol, 55/45 mol/mol (FIG. 3B) and POPC/Triolein (TO), 60/40 mol/mol (FIG. 3C) LNPs dispersed in the absence of $Mn^{2+}$ (upper panels) and in the presence of 2 mM $Mn^{2+}$ (lower panels). LNPs were produced at FRR=3 (3 ml/min for the aqueous stream, 1 ml/min for the ethanolic stream, total lipid concentration in the ethanolic phase 10 mg/ml).

7A. Due to higher downstream resistance, downstream resistance in each layer is essentially identical.

Figure 9:
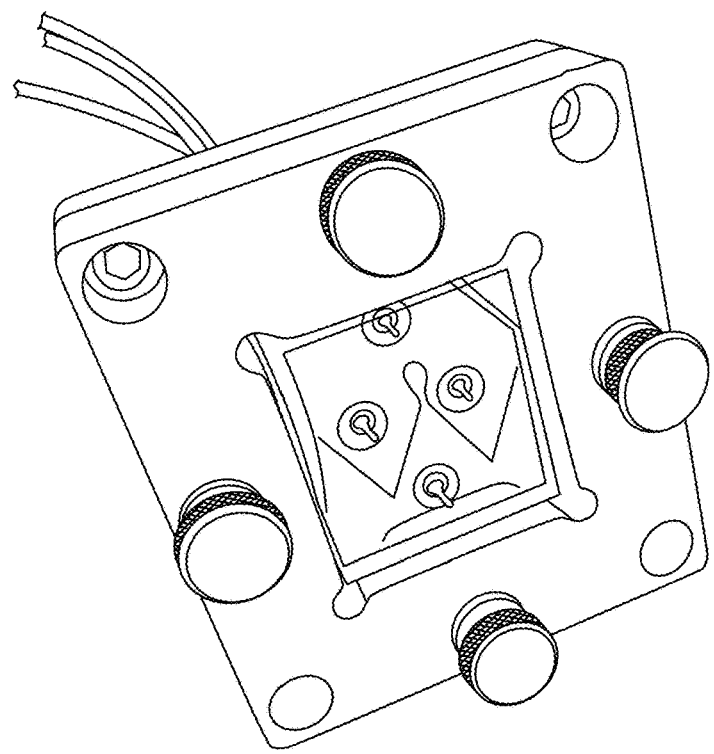

FIG. 9 is an image of a microfluidic scale-up device (chip) loaded into a holder. The device is pressed against the rear surface interface plate and the ports sealed with 0-rings.

Figure 10:
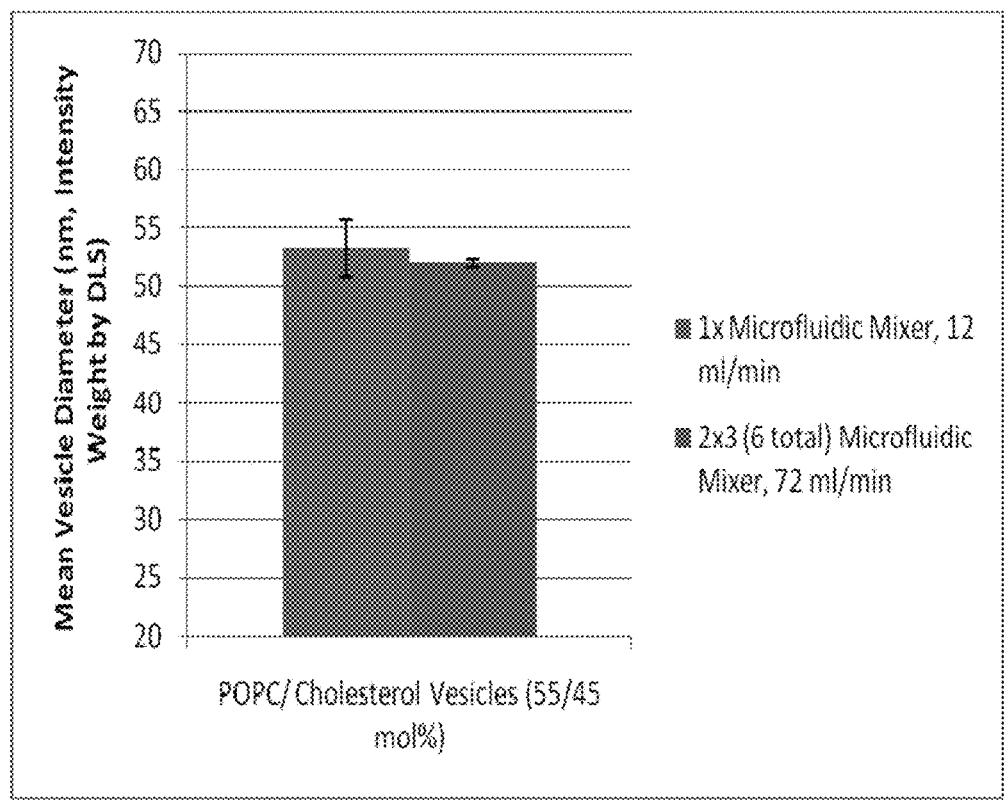

FIG. 10 compares mean vesicle diameter of representative POPC/Cholesterol vesicles (final lipid concentration was 8 mg/mL) prepared by the scale-up system (parallel fluidic device) and a single mixer device.

Figure 11:
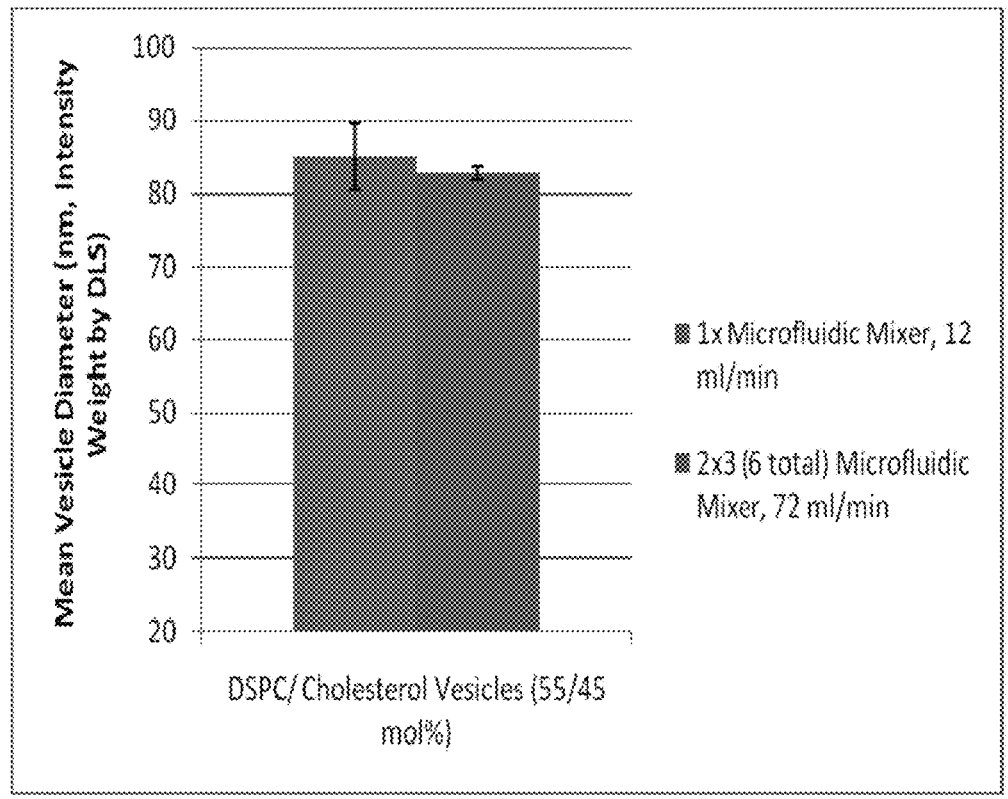

FIG. 11 compares mean vesicle diameter of representative DSPC/Cholesterol vesicles (final lipid concentration was 3 mg/mL) prepared by the scale-up system (parallel fluidic device) and a single mixer device.

Figure 12:
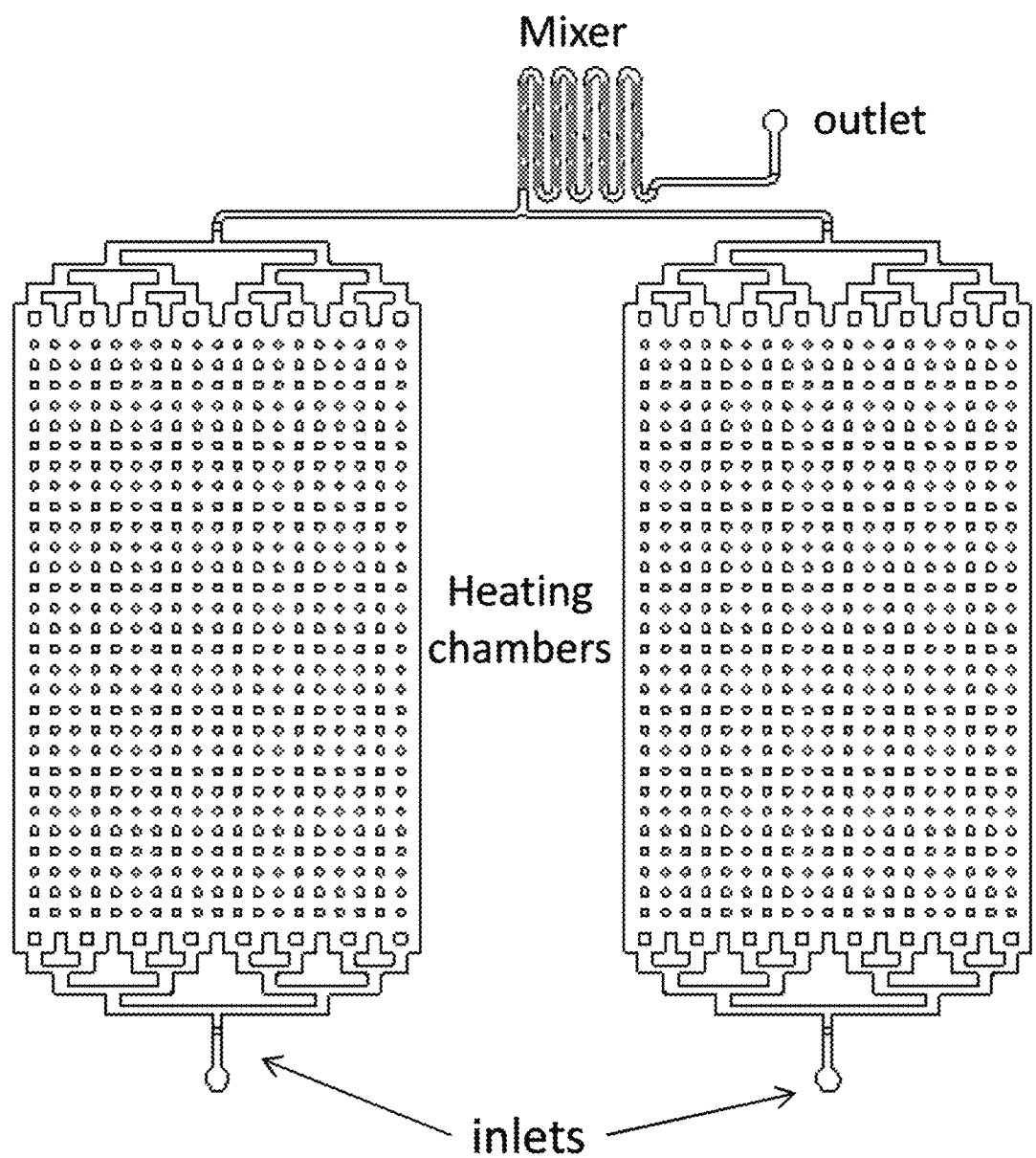

FIG. 12 is a representative temperature-controlled fluid device of the invention having heating chambers.

Figure 13:
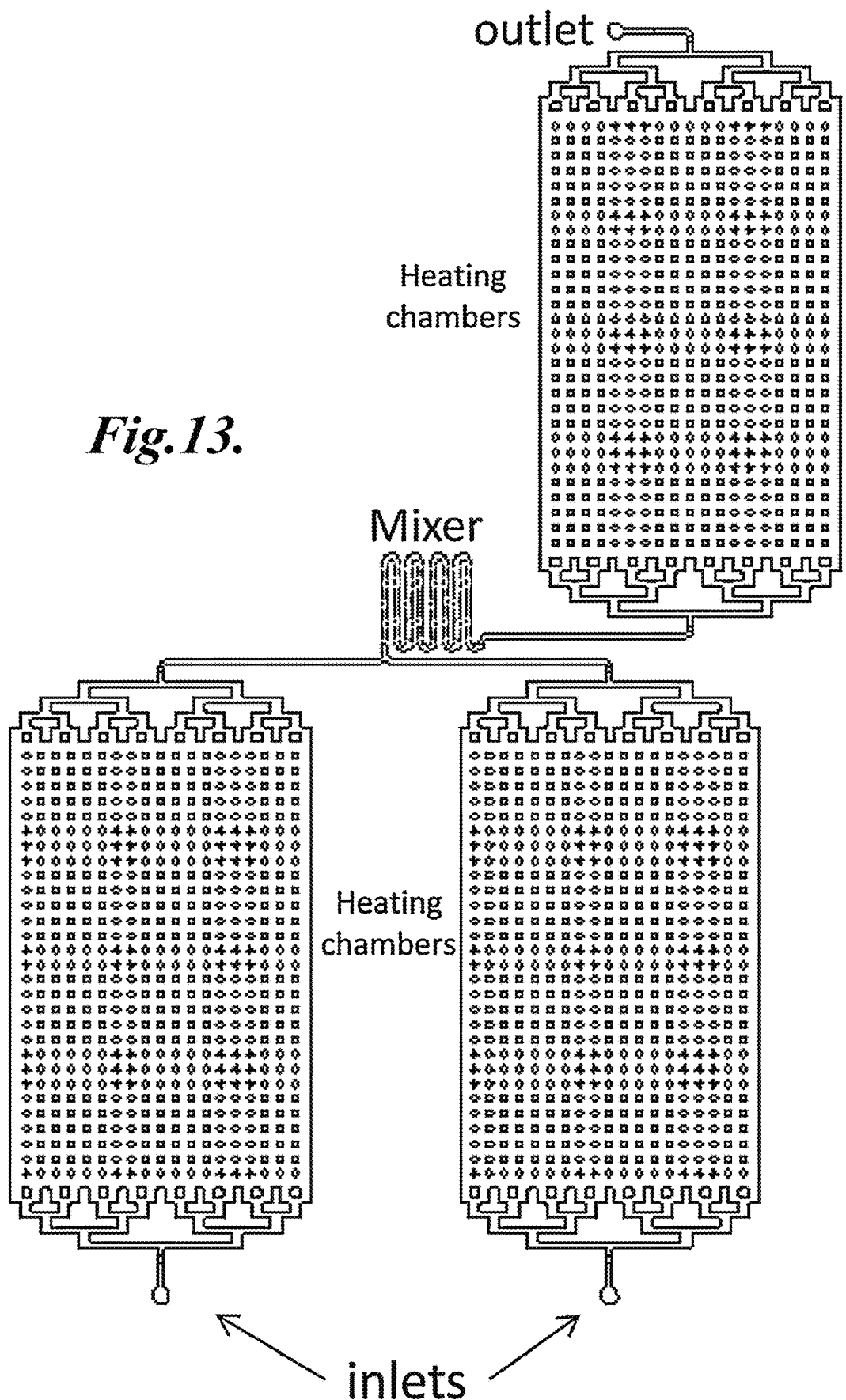

FIG. 13 is a representative temperature-controlled fluid device of the invention having heating chambers.

Figure 14:
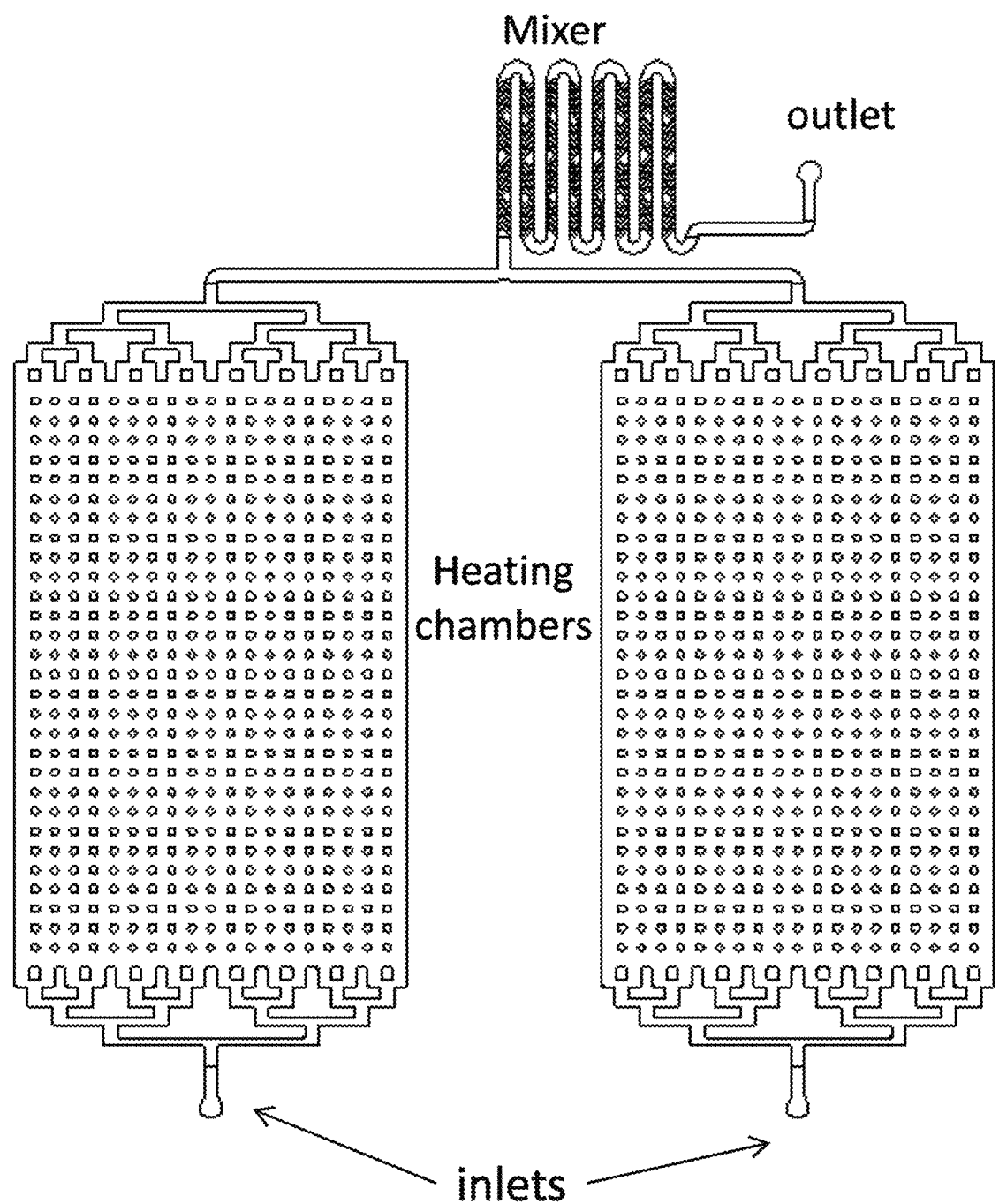

FIG. 14 is a representative temperature-controlled fluid device of the invention having heating chambers.

Figure 15:
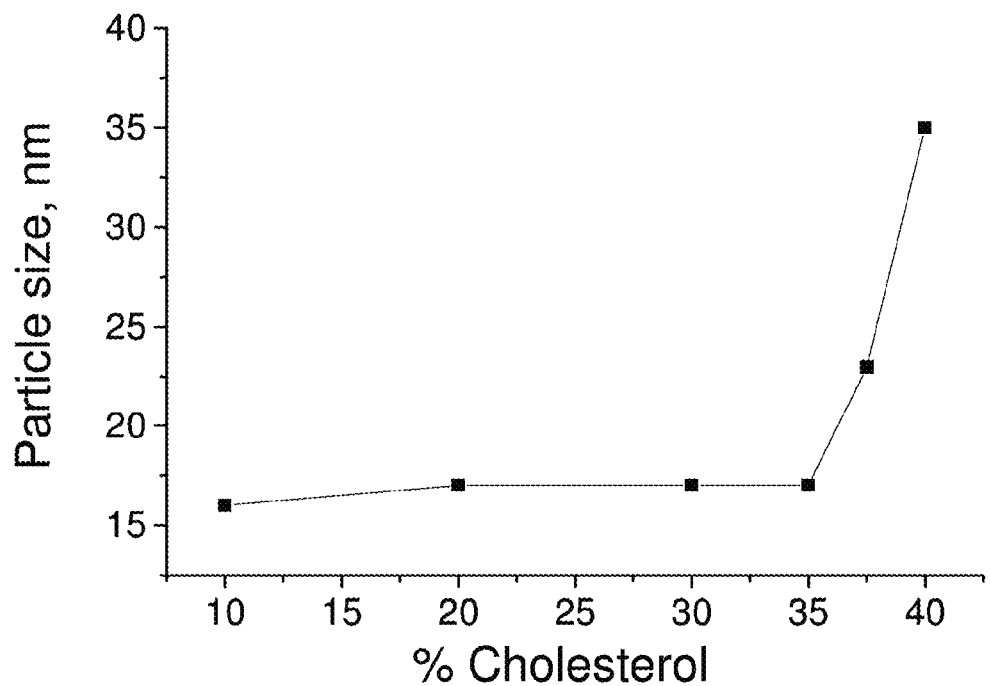

FIG. 15 compares particle size (nm) as a function of mole percent cholesterol (Chol) in a representative lipid bilayer nanoparticle of the invention.

Figure 16:
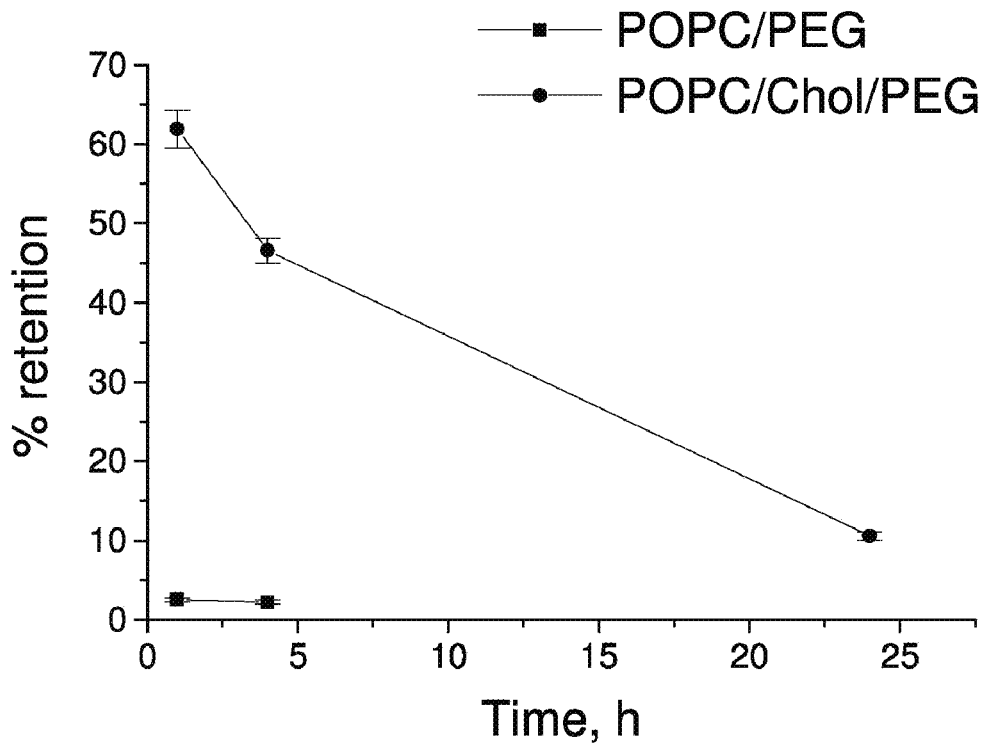

FIG. 16 compares the results of an in vivo pharmacokinetic (PK) study evaluating of retention properties of POPC and POPC/Chol (7:3) DOX loaded systems both containing 6.5% DSPE-PEG2000 (PEG) in plasma of CD-1 mice.

Figure 17:
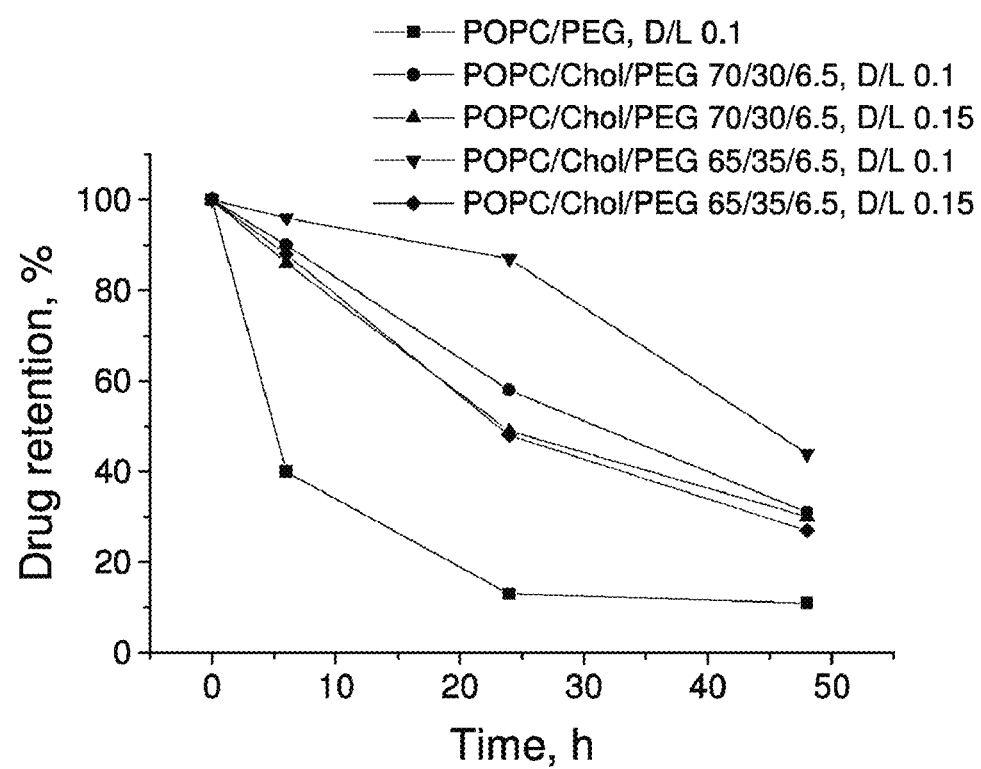

FIG. 17 compares the results of an in vitro release study performed in presence of 50% FBS: POPC/PEG (D/L 0.1), POPC/Chol/PEG 70/30/6.5 (D/L 0.1), POPC/Chol/PEG 70/30/6.5 (D/L 0.15), POPC/Chol/PEG 65/35/6.5 (D/L 0.1), and POPC/Chol/PEG 65/35/6.5 (D/L 0.15).

DETAILED DESCRIPTION

The present invention provides limit size lipid nanoparticles, methods for using the nanoparticles, and methods and systems for making the nanoparticles.

Limit Size Lipid Nanoparticles

In one aspect of the invention, limit size lipid nanoparticles are provided. As used herein the term "limit size" refers to the lowest size limit possible for a particle. The limit size of a particle will depend on the particle's composition, both the particle's components and their amounts in the particle. Limit size lipid nanoparticles are defined as the smallest, energetically stable lipid nanoparticles that can be prepared based on the packing characteristics of the molecular constituents.

In one aspect, limit size lipid nanoparticles are provided in which the lipid nanoparticle has a diameter from about 10 to about 100 nm.

The limit size lipid nanoparticles of the invention include a core and a shell comprising a phospholipid surrounding the core. In certain embodiments, the core includes a lipid (e.g., a fatty acid triglyceride) and is semi-solid, or solid. In other embodiments, the core is liquid (e.g., aqueous). In one embodiment, the shell surrounding the core is a monolayer. In another embodiment, the shell surrounding the core is a bilayer.

In certain embodiments, the limit size nanoparticle includes a lipid bilayer surrounding an aqueous core. The nanoparticles can be advantageously loaded with water-soluble agents such as water-soluble therapeutic and diagnostic agents, and serve as drug delivery vehicles.

The lipid bilayer (or shell) nanoparticle includes a phospholipid. Suitable phospholipids include diacylphosphatidylcholines, diacylphosphatidylethanolamines, ceramides, sphingomyelins, dihydrosphingomyelins, cephalins, and cerebrosides. In one embodiment, the phospholipid is a C8-C20 fatty acid diacylphosphatidylcholine. A representative phospholipid is 1-palmitoyl-2-oleoyl phosphatidylcholine (POPC). In these embodiments, the nanoparticles include from about 50 to about 99 mole percent phospholipid.

In certain embodiments, the nanoparticle further comprises a sterol. In these embodiments, the nanoparticles include from about 10 to about 35 mole percent sterol. Representative sterols include cholesterol. In one embodiment, the ratio of phospholipid to sterol (e.g., cholesterol) is 55:45 (mol:mol). In another embodiment, the ratio of phospholipid to sterol is 60:40 (mol:mol). In a further embodiment, the ratio of phospholipid to sterol is 65:35 (mol:mol). In certain embodiments, the ratio of phospholipid to cholesterol is 70:30 (mol:mol).

The nanoparticle of invention can further include a polyethylene glycol-lipid (PEG-lipid). Suitable polyethylene glycol-lipids include PEG-modified lipids such as PEG-modified phosphatidylethanolamines, PEG-modified phosphatidic acids, PEG-modified ceramides, PEG-modified dialkylamines, PEG-modified diacylglycerols, and PEG-modified dialkylglycerols. Representative polyethylene glycol-lipids include DLPE-PEGs, DMPE-PEGs, DPPC-PEGs, and DSPE-PEGs. In one embodiment, the polyethylene glycol-lipid is DSPE-PEG (e.g., DSPE-PEG2000). In these embodiments, the nanoparticle includes from about 1 to about 10 mole percent polyethylene glycol-lipid.

In representative embodiments, the nanoparticle includes from 55-100% POPC and up to 10 mol % PEG-lipid (aqueous core LNPs).

In other embodiments, the lipid nanoparticles of the invention may include one or more other lipids including phosphoglycerides, representative examples of which include phosphatidylcholine, phosphatidylethanolamine, phosphatidylserine, phosphatidylinositol, phosphatidic acid, palmitoyloleoylphosphatidylcholine, lyosphosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid and glycosphingolipid families are useful. Triacylglycerols are also useful.

Representative particles of the invention have a diameter from about 10 to about 50 nm. The lower diameter limit is from about 10 to about 15 nm.

In other embodiments, the limit size nanoparticle includes a lipid monolayer surrounding a hydrophobic core. These nanoparticles can be advantageously loaded with hydrophobic agents such as hydrophobic or difficultly, water-soluble therapeutic and diagnostic agents.

In certain embodiments, the hydrophobic core is a lipid core. Representative lipid cores include fatty acid triglycerides. In these embodiments, the nanoparticle includes from about 30 to about 90 mole percent fatty acid triglyceride. Suitable fatty acid triglycerides include C8-C20 fatty acid triglycerides. In one embodiment, the fatty acid triglyceride is an oleic acid triglyceride (triglyceride triolein).

The lipid monolayer includes a phospholipid. Suitable phospholipids include those described above. In this embodiment, the nanoparticle includes from about 10 to about 70 mole percent phospholipid.

In certain embodiments, the ratio of phospholipid to fatty acid triglyceride is from 20:80 (mol:mol) to 60:40 (mol:mol). Preferably, the triglyceride is present in a ratio less than about 40% and not greater than about 80%.

The limit size lipid nanoparticles of the invention can include one or more therapeutic and/or diagnostic agents. These agents are typically contained within the particle core. The particles of the invention can include a wide variety of therapeutic and/or diagnostic agents.

Suitable therapeutic agents include chemotherapeutic agents (i.e., anti-neoplastic agents), anesthetic agents, beta-adrenaergic blockers, anti-hypertensive agents, anti-depressant agents, anti-convulsant agents, anti-emetic agents, antihistamine agents, anti-arrhytmic agents, and anti-malarial agents.

Representative anti-neoplastic agents include doxorubicin, daunorubicin, mitomycin, bleomycin, streptozocin, vinblastine, vincristine, mechlorethamine, hydrochloride, melphalan, cyclophosphamide, triethylenethiophosphoramide, carmaustine, lomustine, semustine, fluorouracil, hydroxyurea, thioguanine, cytarabine, floxuridine, decarbazine, cisplatin, procarbazine, vinorelbine, ciprofloxacion, norfloxacin, paclitaxel, docetaxel, etoposide, bexarotene, teniposide, tretinoin, isotretinoin, sirolimus, fulvestrant, valrubicin, vindesine, leucovorin, irinotecan, capecitabine, gemcitabine, mitoxantrone hydrochloride, oxaliplatin, adriamycin, methotrexate, carboplatin, estramustine, and pharmaceutically acceptable salts and thereof.

In certain embodiments, the therapeutic agent is an anti-neoplastic agent. In one embodiment, the anti-neoplastic agent is doxorubicin.

In one embodiment, the invention provides a nanoparticle that includes a lipid bilayer surrounding an aqueous core in which the bilayer includes a phospholipid, a sterol, and a polyethylene glycol-lipid, wherein the core comprises a therapeutic or diagnostic agent. In certain embodiments, the nanoparticle is a limit size nanoparticle. In certain embodiments, the nanoparticle has a diameter from about 10 to about 50 nm.

In one embodiment, the invention provides a lipid monolayer surrounding a hydrophobic core in which the monolayer comprises a phospholipid, and the core includes a fatty acid triglyceride and/or a therapeutic or diagnostic agent. In certain embodiments, the nanoparticle is a limit size nanoparticle. In certain embodiments, the nanoparticle has a diameter from about 10 to about 80 nm.

The lipid nanoparticles of the invention are useful for delivering therapeutic and/or diagnostic agents.

In another aspect, the invention provides a method for administering a therapeutic and/or diagnostic agent to a subject. In the method, a nanoparticle of the invention comprising a therapeutic and/or diagnostic agent is administered to the subject.

In another aspect, the invention provides a method for treating a disease or condition treatable by administering a therapeutic agent effective to treat the disease or condition. In the method, a nanoparticle of the invention comprising the therapeutic agent is administered to the subject in need thereof.

Methods for Making Limit Size Lipid Nanoparticles

In a further aspect, the invention provides methods for making limit size lipid nanoparticle. In one embodiment, the invention provides a method for making lipid nanoparticles in a device having a first region adapted for flow of first and second adjacent streams and a second region for mixing the streams, comprising:

(a) introducing a first stream comprising a first solvent (e.g., an aqueous stream) into the device at a first flow rate;

(b) introducing a second stream comprising lipid particle-forming materials in a second solvent into the device at a second flow rate to provide first and second adjacent streams, wherein the first and second solvents are not the same, and wherein the ratio of the first flow rate to the second flow rate is about 2.0 to about 10.0;

(c) flowing the first and second streams from the first region to the second region; and (d) mixing the first and second streams in the second region of the device to provide a third stream comprising lipid nanoparticles.

In one embodiment, the device is a microfluidic device. In certain embodiments, the flow pre-mixing is laminar flow. In certain embodiments, the flow during mixing is laminar flow.

In one embodiment, the lipid nanoparticles are limit size lipid nanoparticles.

In the method, limit size lipid nanoparticles are prepared by rapid mixing of the first and second streams. The formation of limit size nanoparticles depends on, among other factors, the rate of changing the polarity of the solution containing the lipid particle-forming materials (e.g., rapid mixing of two streams with different polarities). In certain embodiments, the rapid mixing is achieved by flow control; control of the ratio of the first flow rate to the second flow rate. In certain embodiments, the ratio of the first flow rate to the second flow rate is greater than 1:1 (e.g., 2:1, 3:1, 4:1, 5:1, 6:1, 7:1, 8:1, 9:1, 10:1, including intermediate ratios). In other embodiments, the rapid mixing is achieved by controlling the composition of the streams. Rapid change in solvent polarity past a critical point results in limit size nanoparticle formation. For example, reducing the ethanol content in the second stream below 100% (increasing aqueous content to greater than 0%) allows for rapid mixing of the streams at flow rate ratios near 1:1.

In certain embodiment, mixing the first and second streams comprises chaotic advection. In other embodiments, mixing the first and second streams comprises mixing with a micromixer. In certain embodiments, mixing of the first and second streams is prevented in the first region by a barrier (e.g., a channel wall, sheath fluid, or concentric tubing). In certain embodiments, the method further includes diluting the third stream with an aqueous buffer (e.g., flowing the third stream and an aqueous buffer into a second mixing structure or dialyzing the aqueous buffer comprising lipid particles to reduce the amount of the second solvent).

In the method, first solvent is an aqueous buffer and the second solvent is a water-miscible solvent (e.g., an alcohol, such as ethanol). In one embodiment, the second solvent is an aqueous alcohol.

A noted above, in certain embodiments, the second stream include lipid particle-forming materials (e.g., lipids as described above). In one embodiment, the second stream comprises a fatty acid triglyceride. In this embodiment, the fatty acid triglyceride can be present in the second stream in an amount from about 30 to about 90 mole percent. Suitable fatty acid triglycerides include C8-C20 fatty acid triglycerides. A representative fatty acid triglyceride is an oleic acid triglyceride (triglyceride triolein).

In certain embodiments, the second stream comprises a phospholipid. The phospholipid can be present in the second stream in an amount from about 10 to about 99 mole percent. In one embodiment, the phospholipid is a diacylphosphatidylcholine. Suitable phospholipids include those described above, such as C8-C20 fatty acid diacylphosphatidylcholines. A representative phospholipid is 1-palmitoyl-2-oleoyl phosphatidylcholine (POPC).

In certain embodiments, the ratio of phospholipid to fatty acid triglyceride is from 20:80 (mol:mol) to 60:40 (mol:mol).

In certain embodiments, the second stream comprises a sterol (e.g., cholesterol). The sterol can be present in the second stream in an amount from about 10 to about 35 mole percent. In one embodiment, the sterol is cholesterol. In some embodiments, the ratio of phospholipid to cholesterol is 55:45 (mol:mol).

In certain embodiments, the second stream comprises a polyethylene glycol-lipid. Suitable polyethylene glycol-lipids include those described above. The polyethylene glycol-lipid can be present in the second stream in an amount from about 1 to about 10 mole percent. A representative polyethylene glycol-lipid is DSPE-PEG (e.g., DSPE-PEG2000).

In one embodiment, the method further comprises loading the lipid nanoparticle with a therapeutic and/or diagnostic agent to provide a lipid nanoparticle comprising the therapeutic and/or diagnostic agent. Alternatively, the first or second streams can include the therapeutic and/or diagnostic agent depending on the agent's solubility.

The present invention provides microfluidic mixing approaches that at high fluid rate ratios can produce LNP systems of limit size for both aqueous core vesicular systems as well as solid core systems containing a hydrophobic fat such as TO.

There are a number of reports using microfluidic devices to generate homogenous emulsions in a controllable manner. These studies employed two immiscible phases (oil and water) and resulted in formation of micron-sized droplets; nano-sized systems were not achieved using these methodologies. Microfluidic approaches for controlled formation of sub-micrometer sized liposomal dispersions have been performed, where liposomes were formed when a stream of lipids dissolved in a water-miscible organic solvent (isopropyl alcohol) was hydrodynamically focused in a microfluidic channel between two aqueous streams. Small unilamellar vesicles with diameters ranging from 50 to 150 nm were formed whose size was dependent on the buffer-to-alcohol ratio. The vesicle size decreased as the alcohol concentration was lowered, buffer-to-alcohol ratios as high as 60:1 were used to achieve the smallest vesicles.

The present invention provides for the formation of LNP with sizes as small as nm using the staggered herringbone micromixer. As in the case of the flow-focused approach, LNP self-assembly is driven by interdiffusion of two miscible phases. The presence of the herringbone mixer results in an exponential increase in surface area between the two fluids with distance traveled, resulting in much faster interdiffusion. This allows formation of limit size vesicular and solid core LNP at aqueous buffer-to-alcohol flow rate ratios as low as 3.

Limit size vesicles in the size ranges 20-40 nm diameter have previously only been achieved by employing extensive sonication of large multilamellar systems. Sonication has numerous disadvantages including sample degradation and contamination. The microfluidic approach, which does not involve appreciable input of energy to disrupt previously formed structures, is considerably gentler and is unlikely to lead to such effects. In addition, in contrast to sonication, the production of limit size vesicular LNP can be readily scaled using the microfluidic approach by assembling a number of mixers in parallel.

There have been numerous studies employing sonication and other techniques attempting to generate solid core nano-emulsion LNP systems containing a hydrophobic lipid core in the size range of 100 nm diameter or less. There are few reports of the production of solid core LNP smaller than approximately 60 nm diameter. Nanoemulsions with diameters below 50 nm are difficult to achieve using existing techniques. Further, while there have been previous efforts using sonication to vary the size of PC/TO mixtures by varying the proportions of these components, these efforts have been frustrated by the production of oil droplets and liposomes. The microfluidic approach of the present invention offers the ability to produce stable lipid nano-emulsions in a size range that has hitherto been inaccessible.

As noted above, LNP in the size range 10-50 nm offer particular advantages in drug delivery applications, as they are much more able to penetrate to extravascular target tissues than larger systems. A major disadvantage of LNP systems (in the 80-100 nm diameter size range) containing anticancer drugs is that while they are able to extravasate in regions of tumors, there is little penetration into tumor tissue itself. Similarly, presently available LNP systems can penetrate tissues exhibiting "fenestrated" endothelia, such as the liver, spleen or bone marrow, but have very limited ability to penetrate into other tissues. The limit size systems available through the microfluidic mixing techniques of the present invention have considerable utility for extending the applicability of LNP delivery technology.

The following is a description of representative methods and systems of the invention.

The present invention provides rapid microfluidic mixing techniques to generate limit size LNP systems using a "bottom up" approach. As used herein, the phrase "bottom up" refers to methods in which the particles are generated by condensation from solution in response to rapidly increasing polarity of the surrounding medium. In one embodiment, LNP were formed using a herringbone continuous flow microfluidic mixing device that achieves chaotic advection to rapidly mix an organic (ethanol) stream which contains the lipids, with an aqueous stream. Representative lipid systems included 1-palmitoyl-2-oleoyl phosphatidylcholine (POPC), POPC/cholesterol (Chol) and mixtures of POPC with the triglyceride triolein (TO). The results demonstrate that by increasing the flow rate ratio (FRR) between the aqueous stream and the ethanol stream, limit size LNP systems can be obtained for pure POPC and mixtures of POPC with Chol and TO.

Furthermore, the size of the limit size POPC/TO dispersions can be varied over the range 20 nm to 80 nm by varying the POPC/TO ratio.

Microfluidic mixing can produce limit size LNP systems at high flow rate ratios. The present invention provides "limit size" systems that constitute the smallest stable LNP systems that can be made consistent with the physical properties and proportions of the lipid components. LNP were formed by mixing an ethanol stream containing dissolved lipid with an aqueous stream in a microfluidic mixer. It was reasoned that the more rapidly the polarity of the medium experienced by the lipids was increased, the smaller the resulting LNP should become until some limit size was reached. Two factors can influence the rate of increase in polarity: (1) the rate of mixing and (2) the ratio of aqueous to ethanol volumes that are being mixed. The rate of mixing in the herringbone micromixer increases with total flow rate. Smaller LNP are generated as the ratio of the aqueous flow rate to the ethanol flow rate (the flow rate ratio, FRR) is increased due to both more rapid mixing and increased dilution effects. In addition, at higher fluid rate ratios the final ethanol concentration is reduced, thus reducing the production of larger LNP due to particle fusion and lipid exchange (Ostwald ripening) after complete mixing is achieved.

Figure 2A:
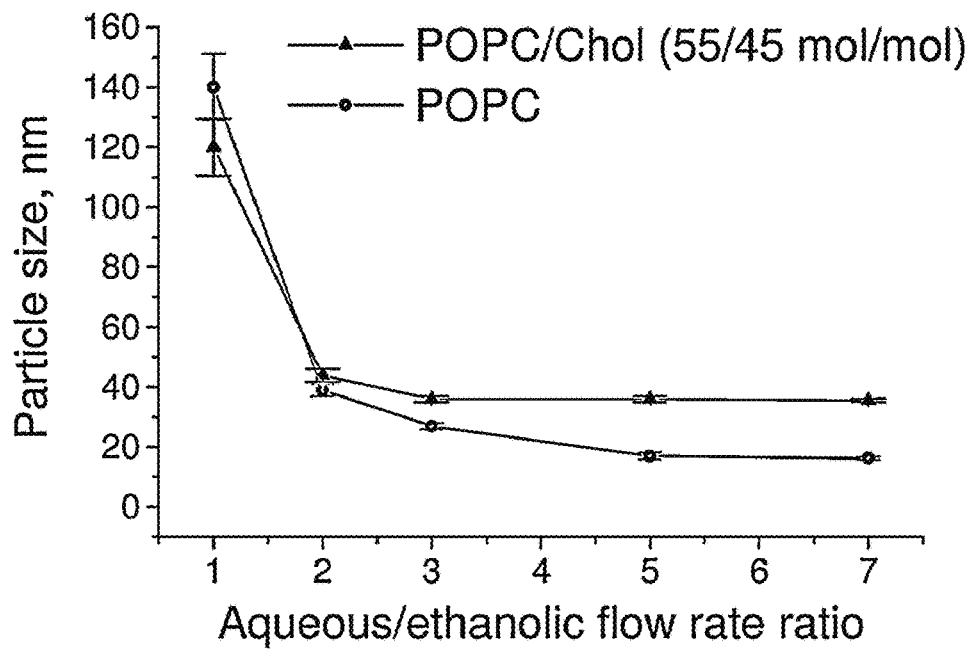
FIGS. 2A and 2B illustrate limit size LNP vesicles (FIGURE A) and phospholipid-stabilized solid-core nanospheres (FIGURE B) produced by increasing the aqueous/ethanolic flow rate ratio (FRR). FRRs were varied by maintaining a constant flow rate in the ethanolic channel (0.5 ml/min) and increasing the flow rates of the aqueous channel from 0.5 to 4.5 ml/min. Size measurements were obtained using DLS (number weighting).

The first set of experiments was designed to determine whether limit size LNP systems could be formed by increasing the FRR using a herringbone microfluidic mixing device. LNPs were formed by mixing ethanol (containing lipids) and aqueous (154 mM saline) streams where the flow rate of the ethanol was held constant (0.5 ml/min) and the flow rate of the aqueous phase was increased over the range 0.5 ml/min to 4.5 ml/min, corresponding to FRR ranging from 1 to 9. The total flow rate was therefore varied over the range 1 ml/min to 5 ml/min Three representative lipid systems were investigated. The first two, POPC and POPC/Chol (55:45; mol/mol) are known to form bilayer vesicles on hydration, whereas the third, mixtures of POPC and triolein (TO), can form "solid core" emulsions with the POPC forming an outer monolayer surrounding a core of the hydrophobic TO. As illustrated in FIG. 2A, for POPC systems, limit size LNP with a diameter of about 20 nm as assayed by dynamic light scattering (DLS; number mode) are observed for 1-KR of 3 and higher. These systems were optically clear, consistent with the small size indicated by DLS. For POPC/Chol mixtures limit size LNP with a diameter of about 40 nm were observed for FRR greater than 2.

Figure 2B:
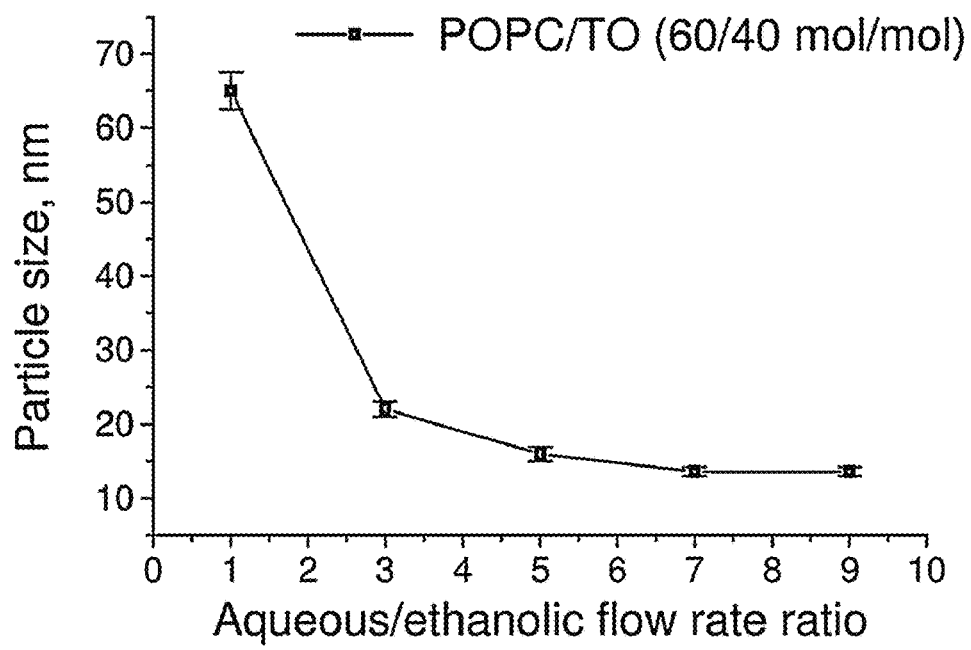

In the case of POPC/TO mixtures the limit size would be expected to be sensitive to the POPC/TO ratio, assuming that the POPC lipids form a monolayer around a solid core of TO. Assuming a POPC area per molecule of 0.7 nm$^2$, a monolayer thickness of 2 nm and a TO molecular weight of 885.4 and density of 0.91 g/ml, a limit particle size of about nm diameter would require a POPC/TO ratio of 60/40 (mol/mol). As shown in FIG. 2B, for FRR of 5 or greater, LNP systems were obtained with a mean particle size of 20 nm for POPC/TO (60/40; mol/mol) mixtures. These small systems were optically clear. It should also be noted that LNP size was highly reproducible (within ±2 nm) between different experiments. No particle size growth for the POPC/TO nanoemulsions incubated at 20° C. in presence of 25% ethanol for at least 24 h was observed (data not shown). Once dialyzed to remove residual ethanol, the POPC/TO 20 nm systems remained stable for at least several months.

Limit size LNP structure as determined by $^{31}$P-NMR studies. $^{31}$P-NMR techniques were used to determine whether some of the phospholipid is sequestered away from the bulk aqueous buffer, which would be consistent with bilayer vesicle structure, or whether all the POPC is in the outer monolayer, which would be consistent with a solid core surrounded by a POPC monolayer. This was straightforward to accomplish because the $^{31}$P-NMR signal arising from the phospholipid in the outer monolayer can be removed by adding $Mn^{2+}$. $Mn^{2+}$ acts as a broadening agent that effectively eliminates the $^{31}$P-NMR signal of phospholipid to which it has access. In the case of small unilamellar vesicles, this corresponds to the outer monolayer, where the $^{31}$P-NMR signal is reduced by 50% or more upon addition of $Mn^{2+}$. In the case of solid core systems, on the other hand, where all the phospholipid should be on the outer monolayer, a complete elimination of signal would be expected on exposure to $Mn^{2+}$.

Figure 3A:
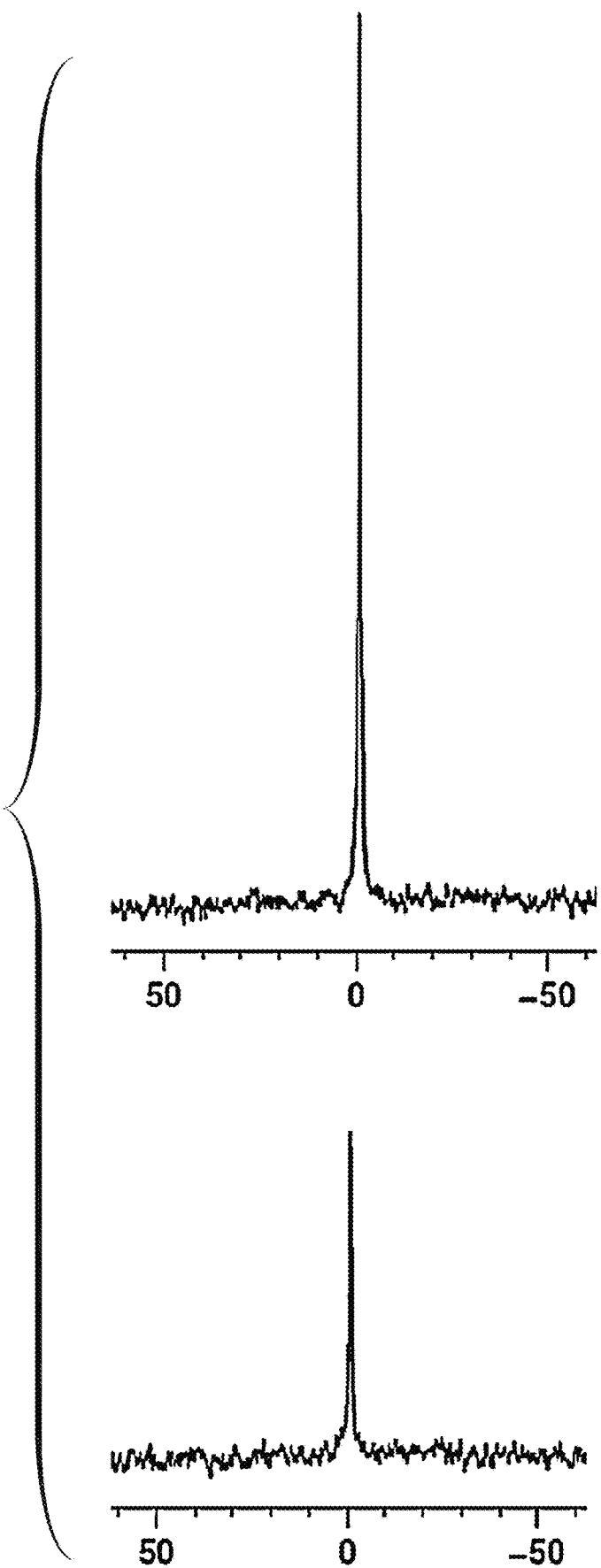
Figure 3C:
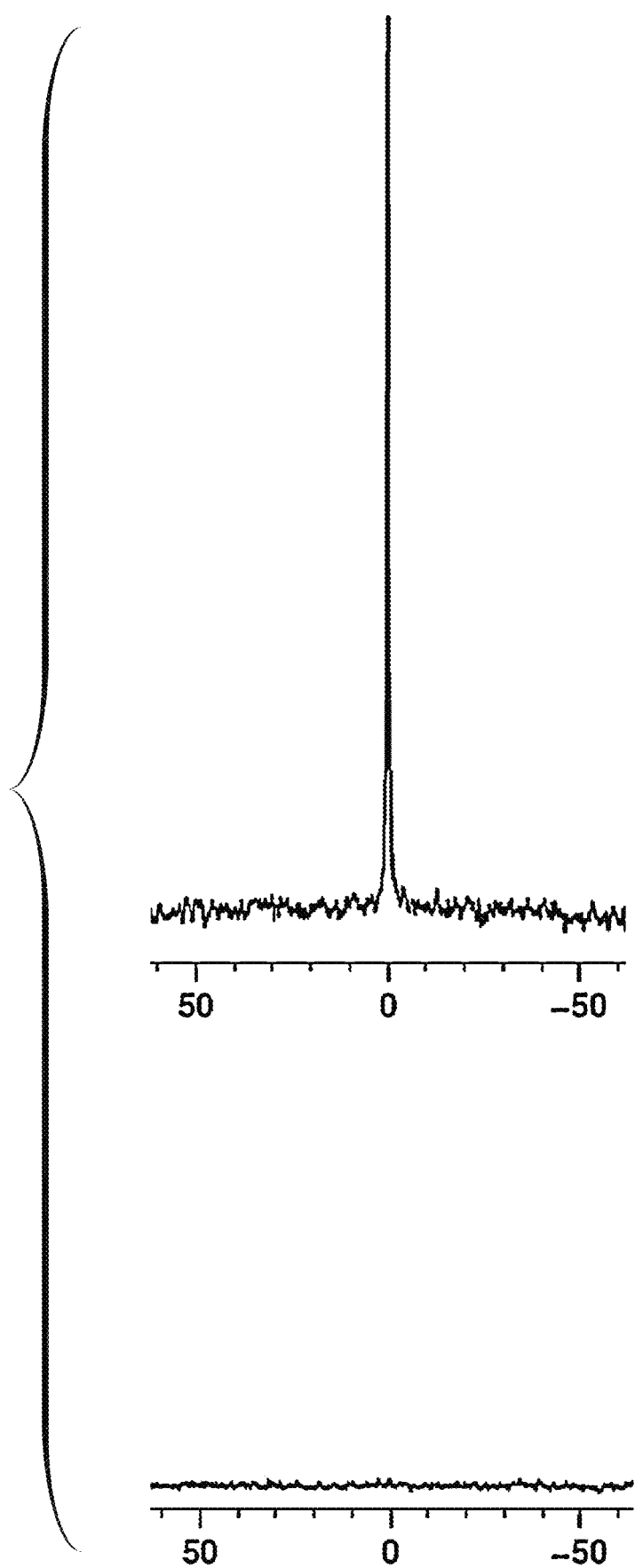

FIGS. 3A-3C illustrate the $^{31}$P NMR spectra obtained for POPC (FIG. 3A), POPC/Chol, 55/45 mol/mol (FIG. 3B) and POPC/TO, 60/40 mol/mol (FIG. 3C) LNP systems in the absence and presence of 2 mM $Mn^{2+}$. As expected, when the buffer contains no $Mn^{2+}$, a sharp "isotropic" peak is observed in all three preparations (upper panels), consistent with rapid isotropic motional averaging effects due to vesicle tumbling and lipid lateral diffusion effects. The addition of $Mn^{2+}$ reduces the signal intensity to levels 50% of the initial signal for the POPC and POPC/Chol systems (FIGS. 3A and 3B, lower panels), indicating the presence of very small unilamellar vesicles. The ratio of the lipid on the outside of the vesicle to the lipid on the inside (Ro/i) can be used to determine the vesicle size if the bilayer thickness and area per lipid molecule is known. The Ro/i for the POPC and POPC/Chol system was calculated from FIGS. 3A and 3B and found to be 1.7 and 1.35, respectively, corresponding to sizes of approximately 30 nm and 50 nm diameter, respectively, assuming a bilayer thickness of 3.5 nm. These values are larger than determined by DLS, which could arise due to increased packing density in the inner monolayer and/or the presence of a small proportion of multilamellar vesicles.

In the case of the POPC/TO (60/40; mol/mol) LNP system, addition of the broadening reagent results in the complete elimination of the $^{31}$P-NMR signal (FIG. 3C, lower panel) in agreement with a TO core system where all the POPC is located in the outer monolayer. There is no evidence of a population of bilayer vesicles as no residual signal from POPC on vesicle interior is detected.

Figure 4A:
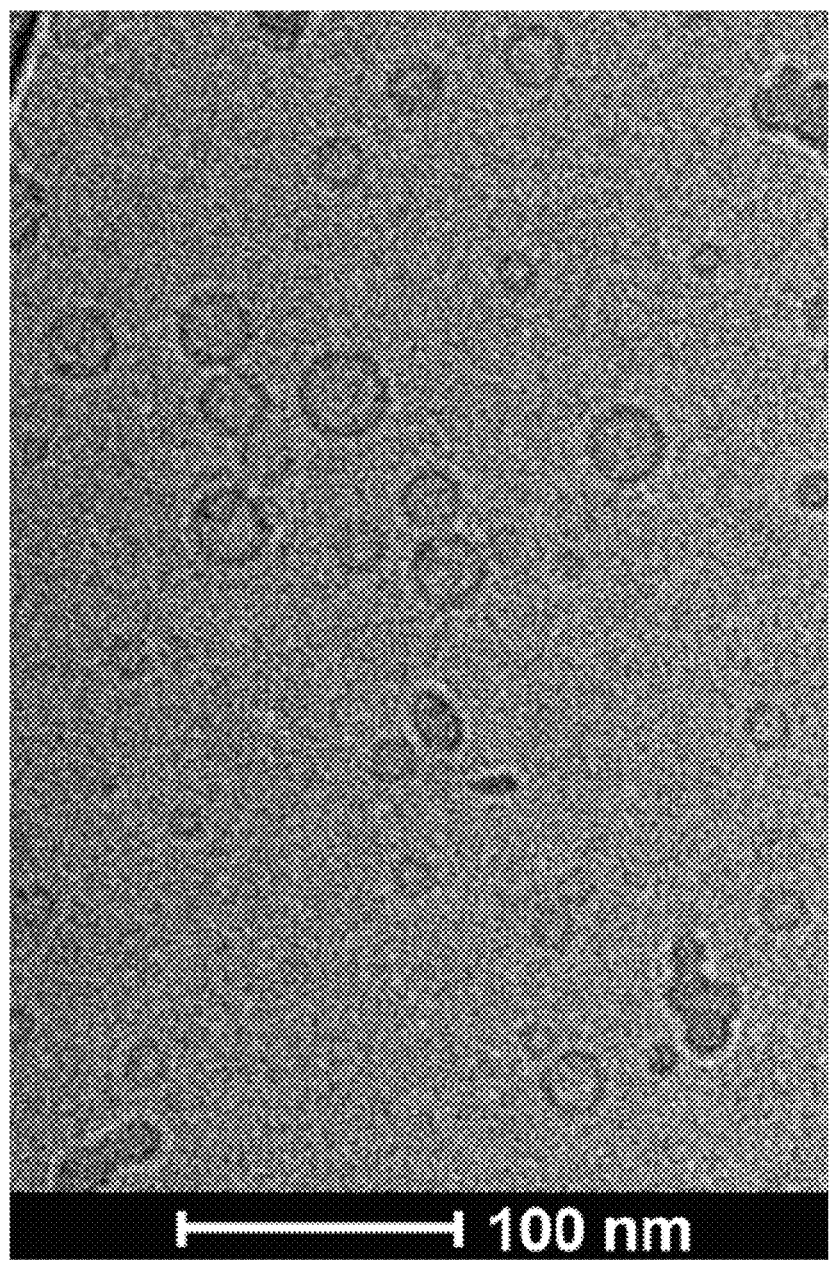
FIGS. 4A-4C are cryo-TEM micrographs of POPC (FIG. 4A), POPC/Chol (FIG. 4B), and POPC/TO (FIG. 4C) LNPs produced at FRR=3 (3 ml/min for the aqueous stream, 1 ml/min for the ethanolic stream, total lipid concentration in the ethanolic phase 10 mg/ml).
Figure 4B:
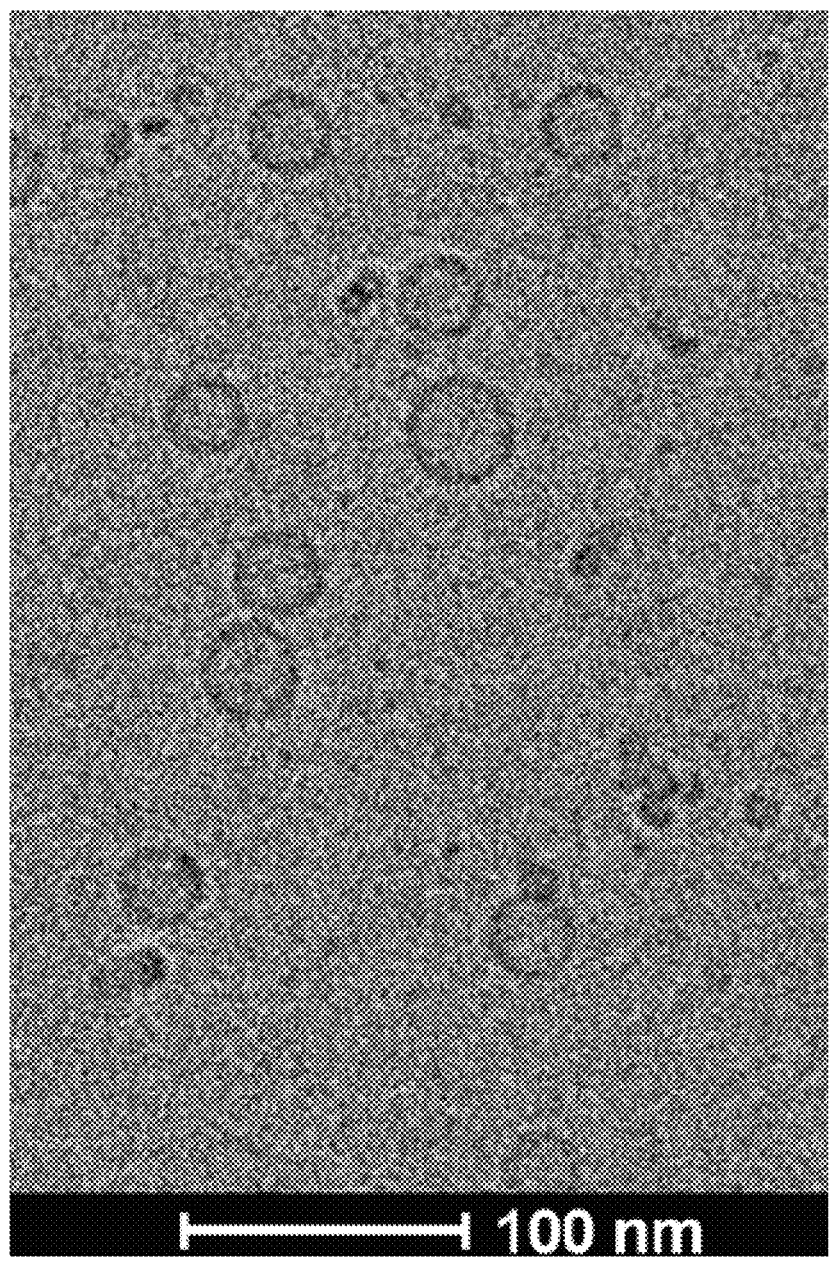
Figure 4C:
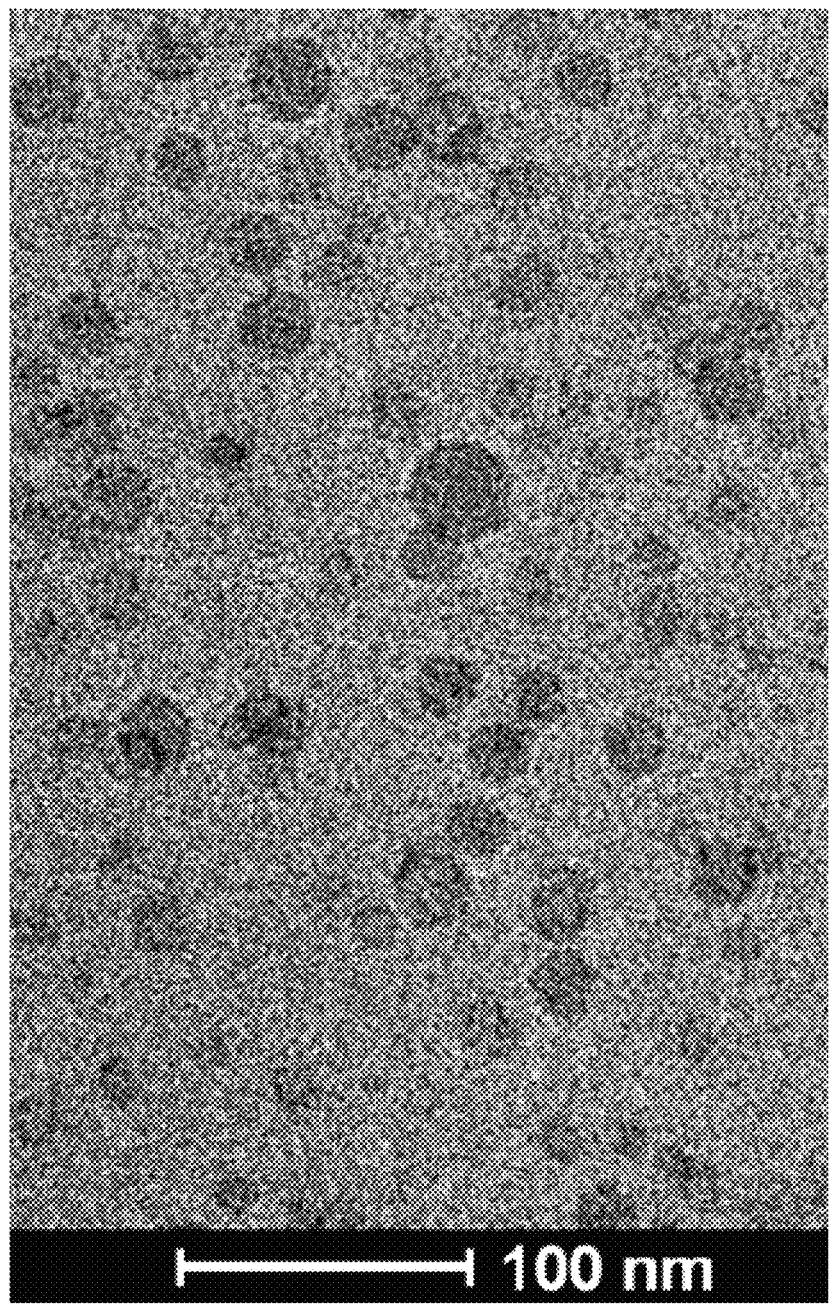

Cryo-transmission electron microscopy studies of LNP size and structure. To confirm formation of LNPs of different sizes and morphology, POPC, POPC/Chol, and POPC/TO systems were visualized using cryo-TEM. The micrographs show the POPC and POPC/Chol systems to have a vesicular morphology with sizes range 15-25 nm (FIG. 4A) and 25-45 nm (FIG. 4B), consistent with the DLS and $^{31}$P-NMR data. In the case of POPC/TO dispersions, cryo-TEM reveals the presence of spherical electron-dense particles with sizes ranging from 15 nm to 25 nm (FIG. 4C) in a good agreement with the DLS sizing data.

Figure 5:
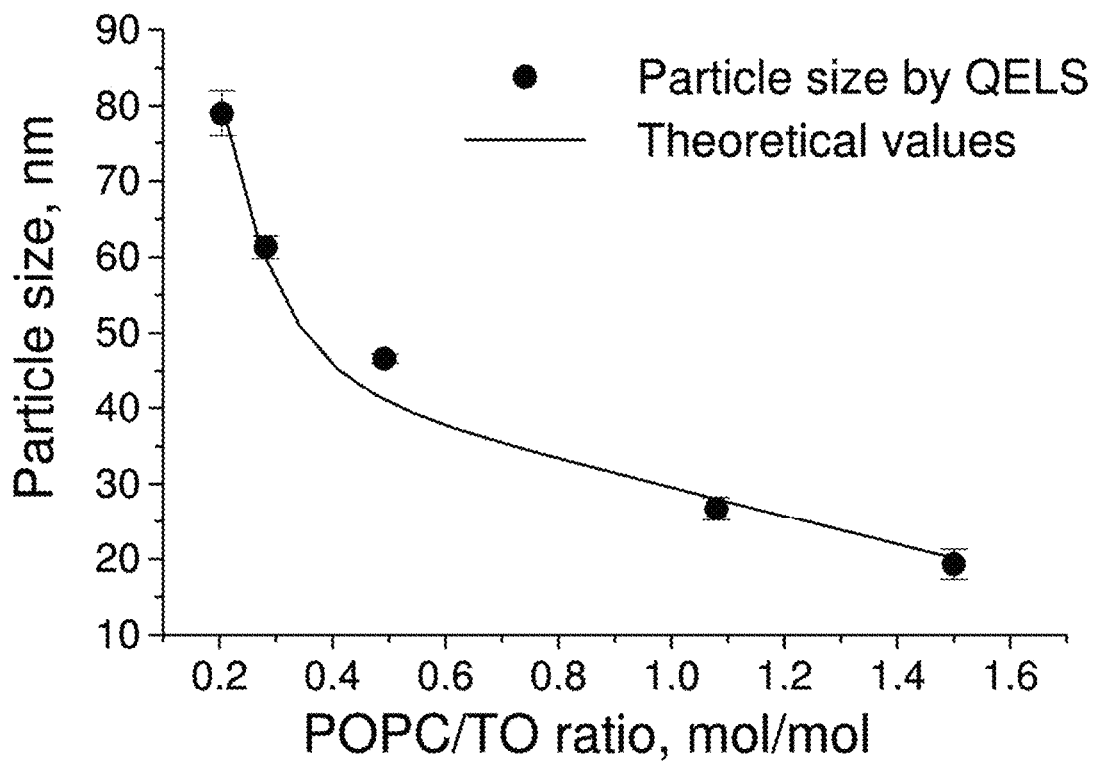
FIG. 5 illustrates the effect of the POPC/TO molar ratio on the size of LNPs. Nanoemulsions based on different POPC/TO ratios (see Table 1) were produced at FRR=3 (3 ml/min for the aqueous stream, 1 ml/min for the ethanolic stream, total lipid concentration in the ethanolic phase 10 mg/ml). The data points for the DLS measured LNP sizes (circles) represent means±SD of 3 experiments. Theoretical values were calculated as described, calculated values were used to plot a curve fit (second order exponential decay).

Influence of POPC/TO ratios on the limit size of LNP produced by microfluidic mixing. As indicated above, the limit size of LNP produced from POPC/TO mixtures should be dependent on the molar ratios of phospholipid to triglyceride. The molar ratios required to form LNP of diameter 20, 40, 60, and 80 nm were calculated and used to produce LNP systems whose size was measured by DLS. FIG. 5 shows the decrease of the mean diameter of the POPC/TO LNPs as a function of POPC/TO molar ratio, compared with the curve that represents the theoretical values. Table 1 provides a direct comparison between predicted and DLS-estimated sizes of POPC/TO LNP. Good correspondence is seen between the predicted size based on the POPC/TO ratio and the actual size.

TABLE 1

Predicted and DLS-estimated sizes of POPC/TO LNP (see FIG. 5).

| Lipid Composition (POPC/TO) | Predicted Diameter (nm) | Actual Diameter (nm) |
| --- | --- | --- |
| 60/40 | 19 | 19.3 ± 2 |
| 52/40 | 30 | 26.7 ± 1.5 |
| 33/67 | 40 | 46.6 ± 0.6 |
| 22/78 | 60 | 61.3 ± 1.5 |
| 17/83 | 80 | 79 ± 3 |

Doxorubicin can be loaded and retained in limit size vesicular LNP. In one aspect of the invention, therapeutic drugs and diagnostic agents can be loaded and retained in limit size vesicular LNP systems. The low trapped volumes of such systems would be expected to limit encapsulation of solutes (such as ammonium sulphate) that can be used to drive the pH gradients (inside acidic) that lead to accumulation of weak base drugs such as doxorubicin. Doxorubicin, a widely used anti-neoplastic agent, was chosen as a model compound as it can be readily accumulated in conventional 100 nm liposomal systems exhibiting a pH gradient. LNP systems composed of POPC containing ammonium sulfate were prepared as below. No significant change in size compared to POPC systems prepared in saline was observed. After removal of the external ammonium sulphate, the ammonium sulfate-containing LNP were incubated at 60° C. in presence of the varying amounts of doxorubicin (initial drug/lipid (D/L) ratios were set at 0.05, 0.1 and 0.2 mol/mol). In all cases, drug loading efficacies approaching 100% were achieved within 30 min (data not shown). DLS analyses of the loaded samples showed no particle size increase compared to the empty precursors (about 20 nm).

Figure 6A:
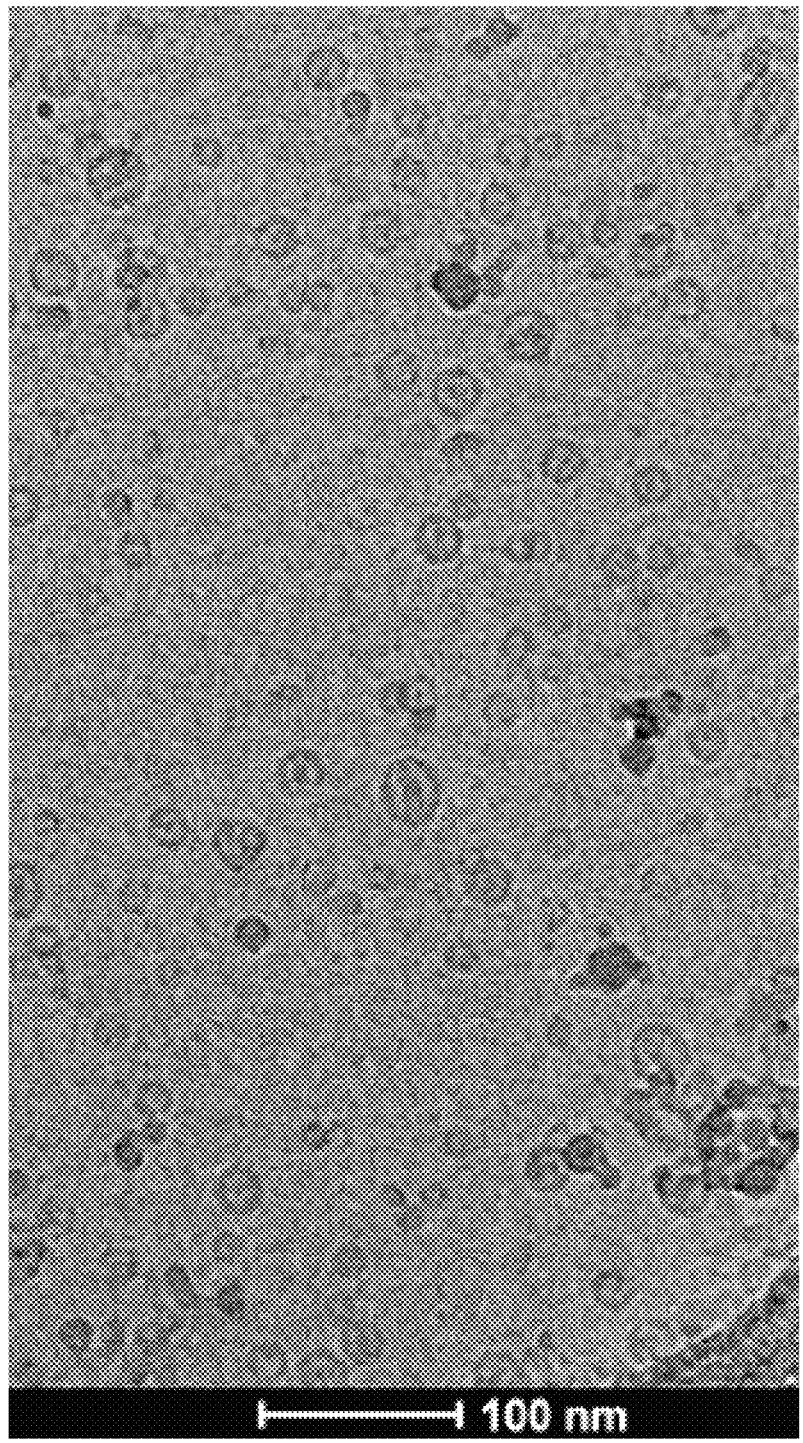
FIGS. 6A and 6B are cryo-TEM micrographs of POPC LNPs loaded with doxorubicin at 0.1 mol/mol (FIG. 6A) and 0.2 mol/mol (FIG. 6B) D/L ratios.
Figure 6B:
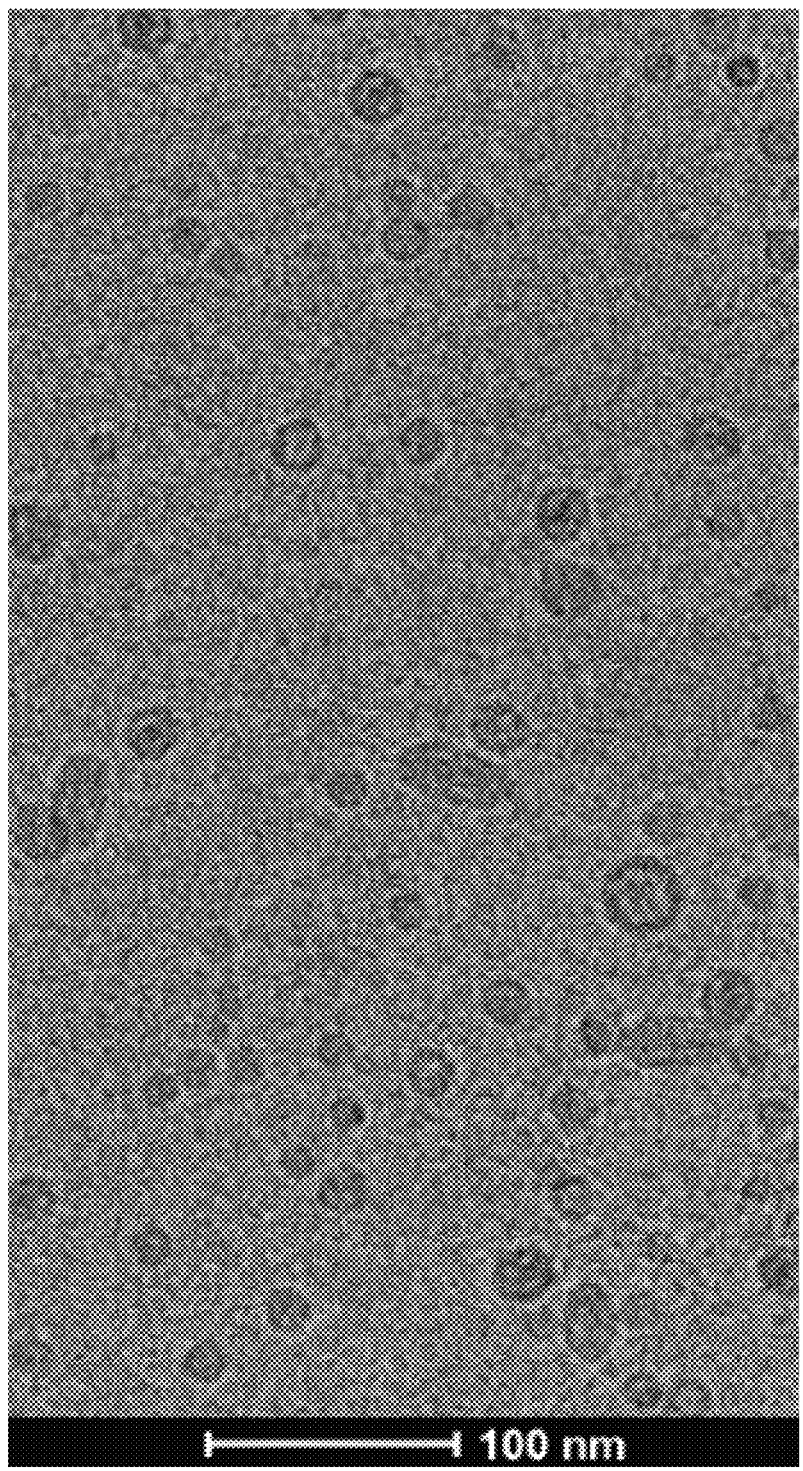

To further investigate the effects of doxorubicin loading on the morphology of the drug-loaded LNP, a cryo-TEM study on POPC LNP loaded at D/L 0.1 and 0.2 mol/mol was performed. Representative images from the cryo-TEM studies are shown in FIGS. 6A and 6B. Previous cryo-TEM studies of liposomal doxorubicin formulations have demonstrated the existence of linear precipitates of encapsulated drug resulting in a "coffee bean" shaped liposomal morphology. Here, LNPs loaded at D/L 0.1 exhibit a similar appearance, indicating the drug precipitation pattern similar to that observed in the 100 nm systems (FIG. 6A). However, at the higher D/L ratio of 0.2 mol/mol the interior of the vesicles appears to be more uniformly electron dense, with the precipitated doxorubicin appearing to coalesce into an amorphous precipitate with no clearly defined structural organization (FIG. 6B); some particles appear elongated in shape. Nonetheless, most of the particles remain spherical; a size analysis of the particles in these micrographs (based on the unbiased sample of about 150) indicated a size of 22±8 nm and 22±10 nm (mean±SD) for the LNP loaded at 0.1 mol/mol and 0.2 mol/mol, respectively.

With the limit size systems exhibiting a high surface/volume ratio and very small radius of membrane curvature, the ability of the loaded LNP to stably retain the encapsulated drug may be a concern. In that regard, the stability of the doxorubicin-loaded LNP stored at 4° C. was monitored for the period of 8 weeks. No detectable drug release/particle size change was observed. For samples incubated at 37° C., 90% (0.1 mol/mol systems) and 75% (0.2 mol/mol systems) of the loaded drug remained encapsulated at 24 h time point (data not shown). These results indicate that ability of the encapsulated drug to form sparingly soluble intravesicular precipitates can be one of the factors that can help to render the drug-loaded limit size LNP adequately retentive.

In certain embodiments, the presence of a sterol and a polyethylene glycol-lipid in the lipid nanoparticle improved the size characteristics of the nanoparticle (e.g., maintained advantageous particle size of from about 15 to about 35 nm. Using the device illustrated schematically in FIG. 1, phosphate buffered saline (pH 7.4) was introduced into one inlet (102) and lipid (DSPC/Chol with or without DSPE-PEG2000) in ethanol was introduced into the second inlet (106). Each was heated to about 60° C. prior to introduction to the device. The total flow rate was 4 mL/min, the FRR was 5:1 (3.33 mL/min aqueous, 0.66 mL/min ethanol), and the initial concentration of lipid in ethanol was 20 mM. The product was dialyzed overnight in phosphate buffered saline at pH 7.4 and the concentrated by Amicon Ultra Centrifugation units (10K MWCO). The results are presented in Tables 2 and 3.

TABLE 2

DSPC/Chol 55/45 (mol %) (average of n = 3 replicates)

| Condition | Int. Wt. (nm) | Num. Wt. (nm) | PDI | Concentration Factor | Concentration (mg/mL) |
| --- | --- | --- | --- | --- | --- |
| Post-dialysis | 56.9 | 48.2 | 0.04 | — | 3 |
| Concentration | 68.9 | 49.5 | 0.09 | 17 | 50 |

TABLE 3

DSPC/Chol/PEG (50/45/5 mol %) (average of n = 3 replicates)

| Condition | Int. Wt. (nm) | Num. Wt. (nm) | PDI | Concentration Factor | Concentration (mg/mL) |
| --- | --- | --- | --- | --- | --- |
| Post-dialysis | 45.2 | 23.8 | 0.16 | — | 3.5 |
| Concentration | 60.1 | 22.1 | 0.25 | 14 | 50 |

FIG. 15 compares particle size (nm) as a function of mole percent cholesterol (Chol) in a representative lipid bilayer nanoparticle of the invention. The presence of 3% mol DSPE-PEG2000 allows the size of POPC/Chol/PEG systems to be maintained up to 35% mol Chol). Size was measured by DLS, number weighting.

As noted above, in certain embodiments, the lipid nanoparticles of the invention can be advantageously loaded with therapeutic agents. In a representative example, doxorubicin (DOX) was loaded into POPC/PEG systems (Chol-free) was performed at 60° C. Drug loading efficacies approaching 100% were achieved within 30 min. However, Chol-containing systems (POPC/Chol/PEG) were unstable at this temperature in presence of the drug (system collapse and formation of large aggregates occurred). Thus, loading of doxorubicin into POPC/Chol/PEG systems was performed at 37° C. (3 h, D/L 0.1 mol/mol). 3% PEG were included into formulation at the formation stage, additional 3.5% were post-inserted prior to loading. The presence of cholesterol in the system resulted in improvement of doxorubicin retention (both in vitro and in vivo).

FIG. 16 compares the results of an in vivo pharmacokinetic (PK) study evaluating of retention properties of POPC and POPC/Chol (7:3) DOX loaded systems both containing 6.5% DSPE-PEG2000 (PEG) in plasma of CD-1 mice. The results shows that the system including the polyethylene glycol lipid demonstrates enhanced retention.

FIG. 17 compares the results of an in vitro release study performed in presence of 50% FBS. The systems evaluated were POPC/PEG (D/L 0.1), POPC/Chol/PEG 70/30/6.5 (D/L 0.1), POPC/Chol/PEG 70/30/6.5 (D/L 0.15), POPC/Chol/PEG 65/35/6.5 (D/L 0.1), and POPC/Chol/PEG 65/35/6.5 (D/L 0.15). The results demonstrate that increasing of the Chol content from 30% to 35% provides increased DOX retention and that increasing D/L ratio to 0.15 mol/mol did not lead to any improvement of drug retention.

Devices and Systems for Making Limit Size Nanoparticles

In another aspect, the invention provides devices and systems for making limit size nanoparticles. In one embodiment, the device includes:

(a) a first inlet (102) for receiving a first solution comprising a first solvent;
(b) a first inlet microchannel (104) in fluid communication with the first inlet to provide a first stream comprising the first solvent;
(c) a second inlet (106) for receiving a second solution comprising lipid particle-forming materials in a second solvent;
(d) a second inlet microchannel (108) in fluid communication with the second inlet to provide a second stream comprising the lipid particle-forming materials in the second solvent; and
(e) a third microchannel (110) for receiving the first and second streams, wherein the third microchannel has a first region (112) adapted for flowing the first and second streams and a second region (114) adapted for mixing the contents of the first and second streams to provide a third stream comprising limit size lipid nanoparticles. The lipid nanoparticles so formed are conducted from the second (mixing) region by microchannel 116 to outlet 118.

Figure 1:
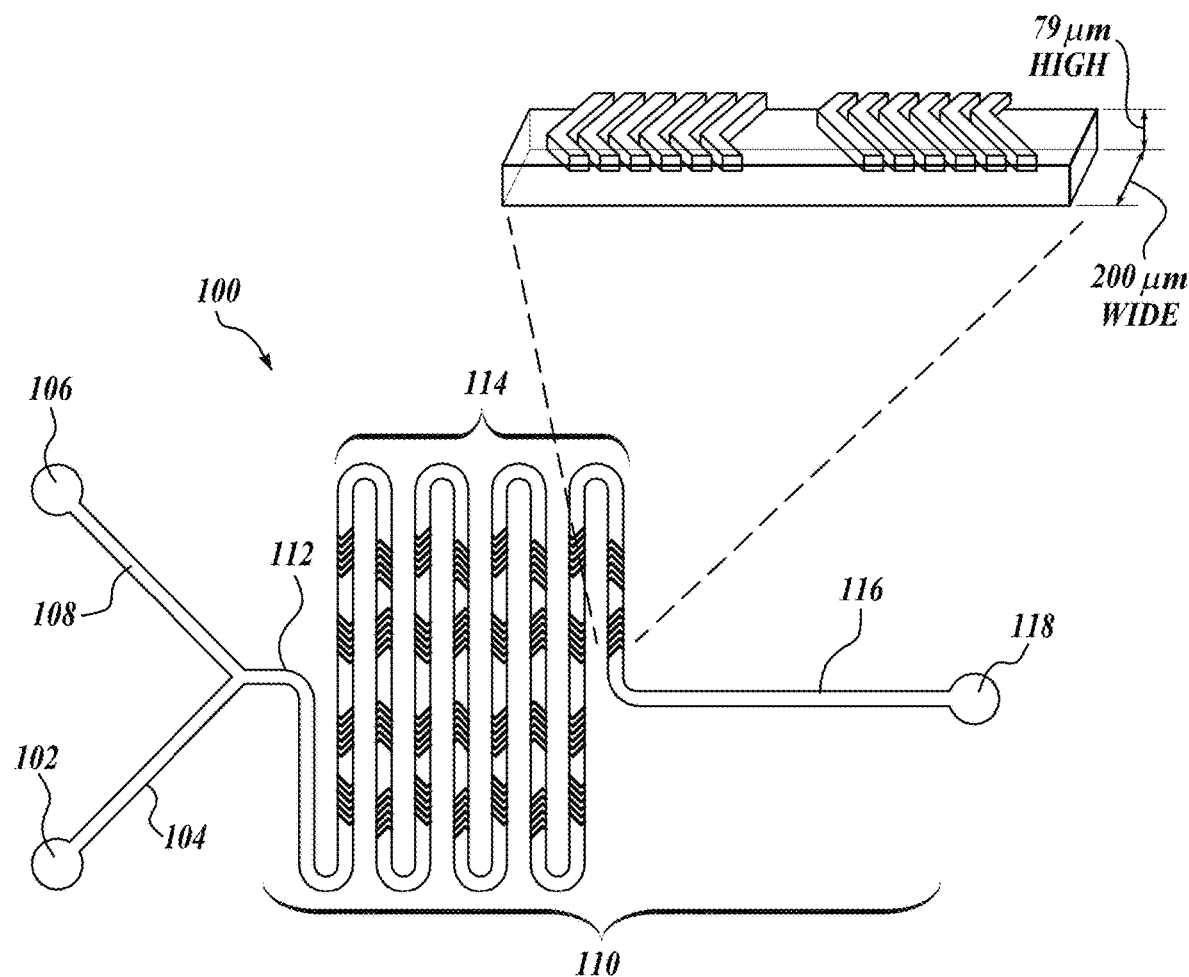
FIG. 1 is a schematic illustration of a representative system of the invention, a continuous-flow staggered herringbone micromixer. The mixing of two separate streams occurs in the patterned central channel which grooved walls drive alternating secondary flows that chaotically stir the fluids injected. The chaotic mixing leads to exponential increase of the interfacial area thus reducing the diffusion distances between two fluids. Rapid interdiffusion of the two phases (aqueous and ethanolic containing fully solvated lipids) results in the self-assembly of LNPs, whose size depends primarily on their lipid composition and aqueous/ethanolic flow rate ratio.

The reference numerals noted above refer to the representative device illustrated schematically in FIG. 1.

In one embodiment, the second region of the microchannel comprises bas-relief structures. In certain embodiments, the second region of the microchannel has a principal flow direction and one or more surfaces having at least one groove or protrusion defined therein, the groove or protrusion having an orientation that forms an angle with the principal direction. In other embodiments, the second region includes a micromixer.

In the devices and systems, means for varying the flow rates of the first and second streams are used to rapidly mix the streams thereby providing the limit size nanoparticles.

In certain embodiments, one or more of the microchannels have a hydraulic diameter from about 20 to about 300 μm.

In certain embodiments, the devices of the invention provide complete mixing occurs in less than 10 ms.

In one embodiment, the device is a parallel microfluidic structure.

In certain embodiments, one or more regions of the device are heated.

Other representative devices and systems for making limit size nanoparticles of the invention are described below.

Parallel Fluidic Structures. In certain aspects, the invention provides devices that include more than one fluidic mixing structures (i.e., an array of fluidic structures). In certain embodiments, the invention provides a single device (i.e., an array) that includes from 2 to about 40 parallel fluidic mixing structures capable of producing lipid nanoparticles at a rate of about 2 to about 1600 mL/min. In these embodiments, the devices produce from 2 to about 20,000 mL without a change in lipid nanoparticle properties.

In one embodiment, the device for producing lipid nanoparticles includes:

(a) a first inlet for receiving a first solution comprising a first solvent;
(b) a first inlet microchannel in fluid communication with the first inlet to provide a first stream comprising the first solvent;
(c) a second inlet for receiving a second solution comprising lipid particle-forming materials in a second solvent;
(d) a second inlet microchannel in fluid communication with the second inlet to provide a second stream comprising the lipid particle-forming materials in the second solvent;
(e) a plurality of microchannels for receiving the first and second streams, wherein each has a first region adapted for flowing the first and second streams and a second region adapted for mixing the contents of the first and second streams to provide a plurality of streams compromising lipid nanoparticles; and
(f) a fourth microchannel for receiving and combining the plurality of streams comprising lipid nanoparticle.

In certain embodiments, each of the plurality of microchannels for receiving the first and second streams includes:

(a) a first microchannel in fluidic communication with the first inlet microchannel to receive the first stream comprising the first solvent;
(b) a second microchannel in fluidic communication with the second inlet microchannel to receive the second inlet stream comprising the second solvent; and
(c) a third microchannel for receiving the first and second streams, wherein each has a first region adapted for flowing the first and second streams and a second region adapted for mixing the contents of the first and second streams to provide a plurality of streams compromising lipid nanoparticles.

In certain embodiments, the device includes from 2 to about 40 microchannels for receiving the first and second streams. In these embodiments, the device has a total flow rate from 2 to about 1600 mL/min.

In certain embodiments, the second regions each have a hydraulic diameter of from about 20 to about 300 μm. In certain embodiments, the second regions each have a fluid flow rate of from 1 to about 40 mL/min.

For embodiments that include heating elements, the heating element is effective to increase the temperature of the first and second streams in the first and second microchannels to a pre-determined temperature prior to their entering the third microchannel. In these embodiments, the inlet fluids are heated to a desired temperature and mixing occurs sufficiently rapidly such that the fluid temperature does not change appreciably prior to lipid nanoparticle formation.

In one embodiment, the invention provides a system for making limit size nanoparticles that includes a parallel microfluidic structure. In a parallel structure, N single mixers are arrayed such that a total flow rate of N×F is achieved, where F is the flow rate used in the non-parallelized implementation. Representative parallel microfluidic structures of the invention are illustrated schematically in FIGS. 7A-7C.

Figure 7A:
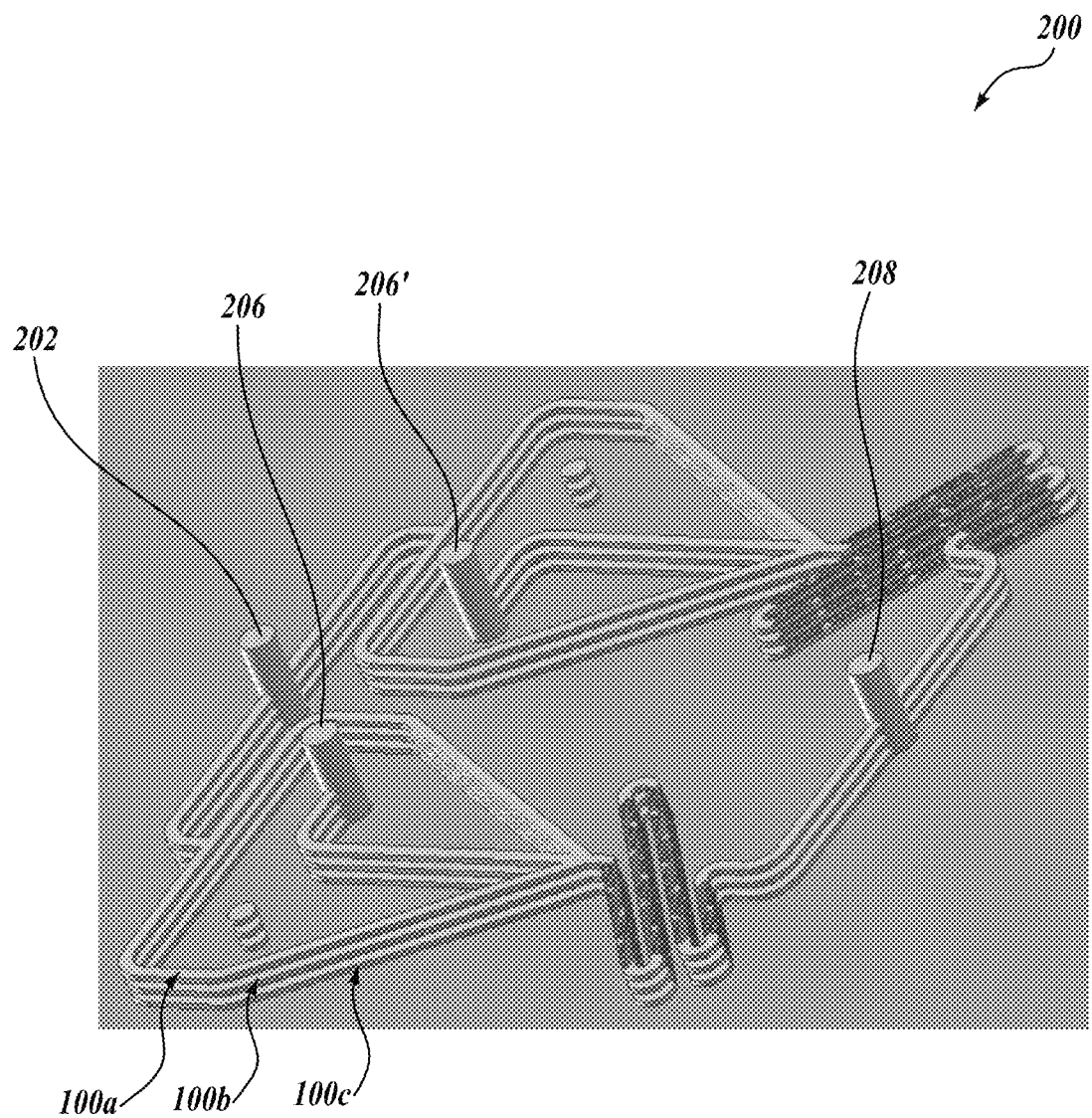
FIG. 7A is a three-dimensional view of a representative parallel fluidic structure of the invention useful for making limit size lipid nanoparticles.
Figure 7B:
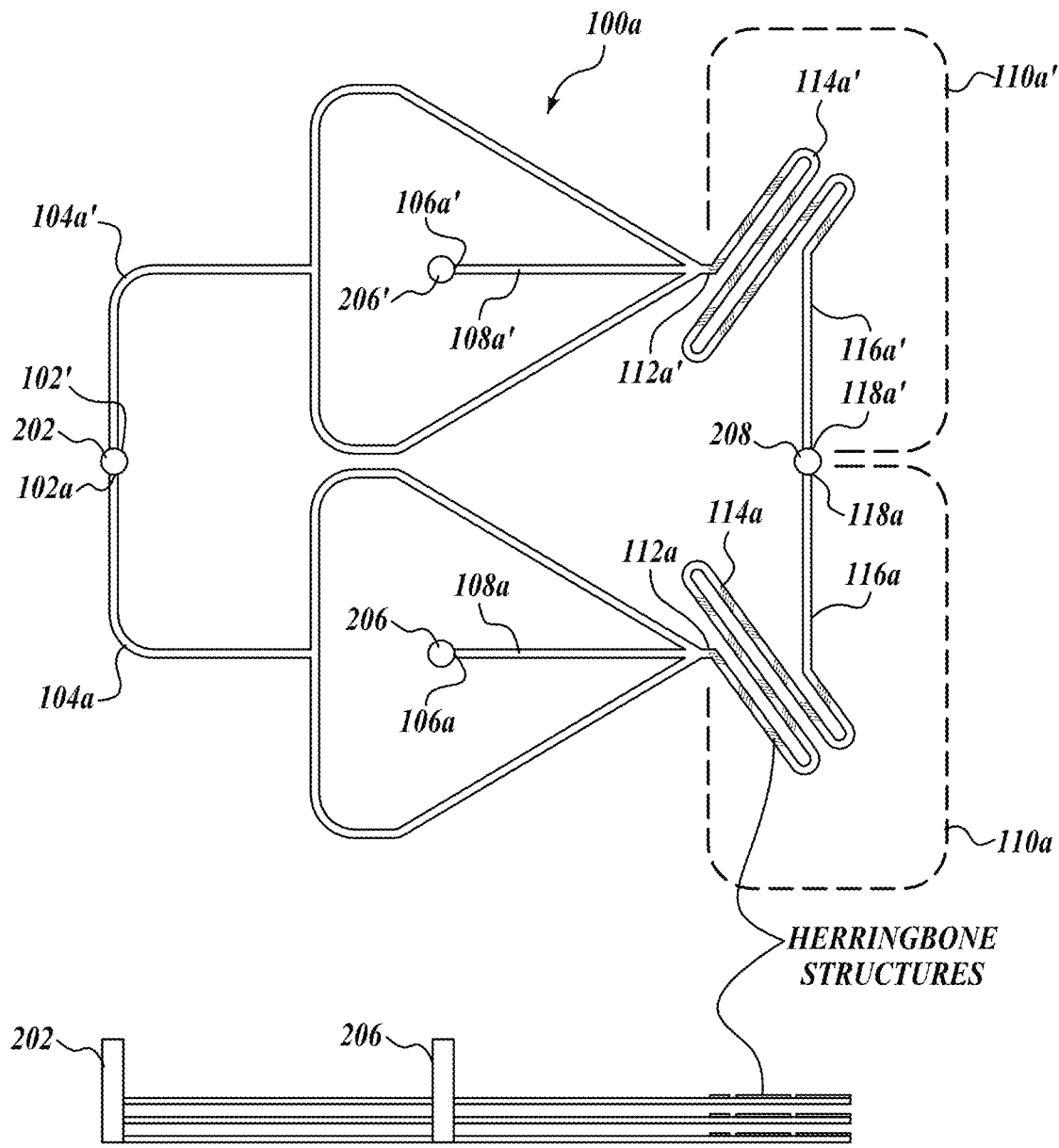
FIG. 7B shows a top view and a side view of the representative parallel fluidic structure shown in FIG. 7A. The top view shows two planar herringbone structures in parallel. The side view shows that the fluidic parallel fluidic structure has three layers to give a total of six herringbone structures.

A perspective view of a representative parallel microfluidic structure is illustrated in FIG. 7A and a plan view is illustrated in FIG. 7B.

Referring to FIG. 7A, device 200 includes three fluidic systems (100a, 100b, and 100c) arranged vertically with each system including one first solvent inlet (202), two second solvent inlets (206 and 206'), two mixing regions (110 and 110'), and a single outlet (208). Each system includes microchannels for receiving the first and second streams (202 and 206 and 206,' respectively).

Referring to FIG. 7B, each fluidic system includes:
(a) a first microchannel (202) in fluidic communication via first inlet (102a) with a first inlet microchannel (104a) to receive the first stream comprising the first solvent;
(b) a second microchannel (206) in fluidic communication via second inlet (106a) with the second inlet microchannel (108a) to receive the second inlet stream comprising the second solvent; and
(c) a third microchannel (110a) for receiving the first and second streams, wherein each has a first region (112a) adapted for flowing the first and second streams and a second region (114a) adapted for mixing the contents of the first and second streams to provide a plurality of streams comprising lipid nanoparticles. In FIG. 7B, microchannel 116a conducts one of the plurality of streams from the mixing region to fourth microchannel 208 via outlet 118a that conducts the lipid nanoparticles from the device.

With reference to FIG. 7B, it will be appreciated that in this embodiment of the device, fluidic system 100a includes a second second solvent inlet (206') and mixing region (110a') with components denoted by reference numerals 102a', 104a', 106a', 108a', 112a', 114a', 116a' and 118a'. These reference numerals correspond to their non-primed counterparts (102, 104, 106, 108, 112, 114, 116, and 118) in FIG. 7B.

This structure produces vesicles at higher flow rates compared to the single mixer chips and produces vesicles identical to those produced by single mixer chips. In this representative embodiment, six mixers are integrated using three reagent inlets. This is achieved using both planar parallelization and vertical parallelization as shown in FIGS. 7A and 7B.

Planar parallelization refers to placing one or more mixers on the same horizontal plane. These mixers may or may not be connected by a fluidic bus channel Equal flow through each mixer is assured by creating identical fluidic paths between the inlets and outlets, or effectively equal flow is achieved by connecting inlets and outlets using a low impedance bus channel as shown in FIG. 7C (a channel having a fluidic impedance significantly lower than that of the mixers).

Figure 7C:
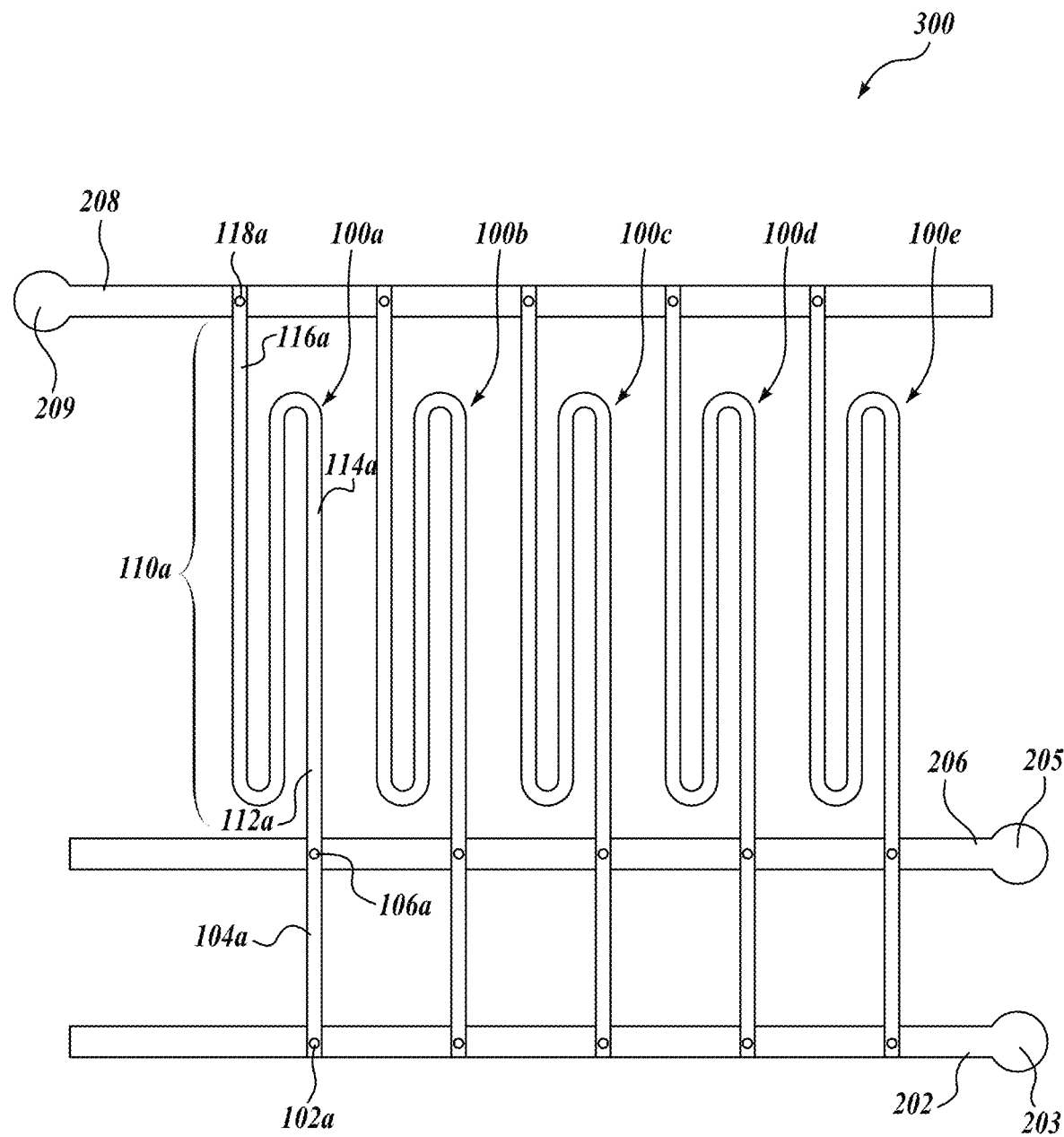
FIG. 7C is a three-dimensional view of a second representative parallel fluidic structure of the invention useful for making limit size lipid nanoparticles.

FIG. 7C illustrates device 300 includes five fluidic systems (100a, 100b, 100c, 100d, and 100e) arranged horizontally with each system including one first solvent inlet, one second solvent inlet, one mixing region, and a single outlet (208). Device 300 includes microchannels for receiving the first and second streams (202 and 206) and a microchannel (208) for conducting lipid nanoparticles produced in the device from the device.

Referring to FIG. 7C, fluidic system 100a includes:
(a) a first microchannel (202) (with inlet 203) in fluidic communication via first inlet (102a) with a first inlet microchannel (104a) to receive the first stream comprising the first solvent;
(b) a second microchannel (206) (with inlet 205) in fluidic communication via second inlet (106a) with inlet microchannel (104a) to receive the second inlet stream comprising the second solvent; and
(c) a third microchannel (110a) for receiving the first and second streams, wherein the third microchannel has a first region (112a) adapted for flowing the first and second streams and a second region (114a) adapted for mixing the contents of the first and second streams to provide a third stream compromising lipid nanoparticles. In FIG. 7C, microchannel 116a conducts the third stream from the mixing region to fourth microchannel 208 via outlet 118a. Microchannel 208 conducts the lipid nanoparticles from the device via outlet 209.

With reference to FIG. 7B, it will be appreciated that in this embodiment of the device, fluidic system 100a includes a second second solvent inlet (206') and mixing region (110a') with components denoted by reference numerals 102a', 104a', 106a', 108a', 112a', 114a', 116a' and 118a'. These reference numerals correspond to their non-primed counterparts (102, 104, 106, 108, 112, 114, 116, and 118) in FIG. 7B.

In one embodiment, the invention provides a device for producing limit size lipid nanoparticles, comprising n fluidic devices, each fluidic device comprising:
(a) a first inlet (102a) for receiving a first solution comprising a first solvent;
(b) a first inlet microchannel (104a) in fluid communication with the first inlet to provide a first stream comprising the first solvent;
(c) a second inlet (106a) for receiving a second solution comprising lipid particle-forming materials in a second solvent; and
(d) a third microchannel (110a) for receiving the first and second streams, wherein the third microchannel has a first region (112a) adapted for flowing the first and second streams and a second region (114a) adapted for mixing the contents of the first and second streams to provide a third stream comprising limit size lipid nanoparticles conducted from the mixing region by microchannel 116a, wherein the first inlets (102a-102n) of each fluidic device (100a-100n) are in liquid communication through a first bus channel (202) that provides the first solution to each of the first inlets, wherein the second inlets (106a-106n) of each fluidic device (100a-100n) are in liquid communication through a second bus channel (206) that provides the second solution to each of the second inlets, and wherein the outlets (118a-118n) of each fluidic device (100a-100n) are in liquid communication through a third bus channel (208) that conducts the third stream from the device. The reference numerals refer to representative device 300 in FIG. 7C.

In certain embodiments, n is an integer from 2 to 40.

Figure 8:
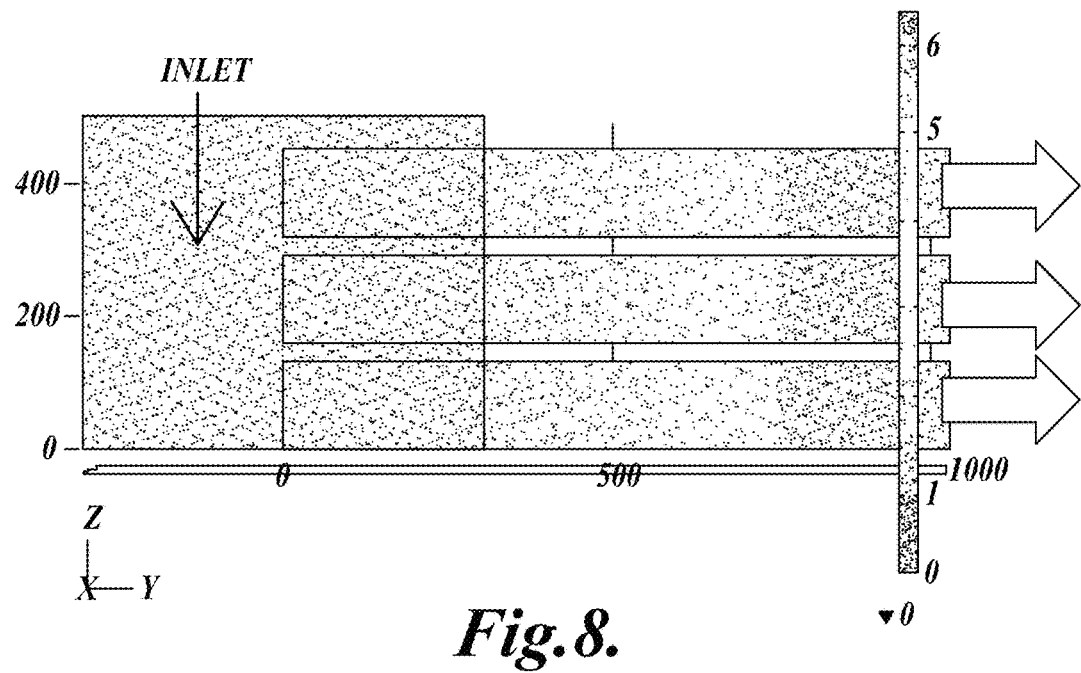
FIG. 8 is an image of the simulated pressure drop between the inlet port and the first section of each layer of the representative parallel fluidic structure shown in FIG.

Vertical parallelization is achieved by forming planar mixers and stacking them together and connecting the inlets and outlets through a vertical bus. Theoretically, fluid flowing from the inlets to the lower mixer encounters a higher resistance than that flowing to the top mixer, therefore leading to a lower flow rate. However, as the distance separating the two mixers is less than 500 microns, the increased resistance is negligible when compared to the overall resistance of the mixing structure (which is identical for each layer). This is confirmed both through the experimental results and through fluid flow simulations (FIG. 8). The distance separating mixing layers for which this condition is true is dependent on the width of the bus.

Parallelized devices are formed by first creating positive molds of planar parallelized mixers that have one or more microfluidic mixers connected in parallel by a planar bus channel. These molds are then used to cast, emboss or otherwise form layers of planar parallelized mixers, one of more layers of which can then be stacked, bonded and connected using a vertical bus channels. In certain implementations, planar mixers and buses may be formed from two separate molds prior to stacking vertically (if desired). In one embodiment positive molds of the 2×planar structure on a silicon wafer are created using standard lithography. A thick layer of on-ratio PDMS is then poured over the mold, degassed, and cured at 80 C for 25 minutes. The cured PDMS is then peeled off, and then a second layer of 10:1 PDMS is spun on the wafer at 500 rpm for 60 seconds and then baked at 80° C. for 25 minutes. After baking, both layers are exposed to oxygen plasma and then aligned. The aligned chips are then baked at 80° C. for 15 minutes. This process is then repeated to form the desired number of layers. Alignment can be facilitated by dicing the chips and aligning each individually and also by making individual wafers for each layer which account for the shrinkage of the polymer during curing.

Using a custom chip holder, this chip has been interfaced to pumps using standard threaded connectors (see FIG. 9). This has allowed flow rates as high as 72 ml/min to be achieved. Previously, in single element mixers, flows about 10 ml/min were unreliable as often pins would leak eject from the chip. In order to interface with these holders, chips are sealed to on the back side to glass, and the top side to a custom cut piece of polycarbonate or glass with the interface holes pre-drilled. The PC to PDMS bond is achieved using a silane treatment. The hard surface is required to form a reliable seal with the o-rings. A glass backing is maintained for sealing the mixers as the silane chemistry has been shown to affect the formation of the nanoparticles.

The devices and systems of the invention provide for the scalable production of limit size nanoparticles. The following results demonstrate the ability to produce identical vesicles, as suggested by identical mean diameter, using the microfluidic mixer illustrated in FIGS. 7A and 7B.

Mean vesicle diameter (nm) for scale-up formulation of representative limit size nanoparticles (DSPC/Cholesterol vesicles) produced using the parallel microfluidic structure is compared to those produced using a single mixer microfluidic device in FIG. 11 (final lipid concentration was 3 mg/mL). Formulation of DSPC/Cholesterol vesicles is made using a 130 μm×300 μm mixer (channel cross-section) by mixing at a buffer:lipid-ethanol volumetric flow rate ratio of 3:1, with a total flow rate of 12 ml/min in a single microfluidic mixer. The scale-up mixer, which enables throughput of 72 ml/min (6×scaling), consists of 6 original mixers where three sets of two mixers are stacked vertically and placed next to each other horizontally. Final lipid concentration after mixing in microfluidic device is 3 mg/ml. Error bars represent standard deviation of multiple formulations made with microfluidic mixer (n=3 for 1×mixer and n=2 for 6×mixer).

Mean vesicle diameter (nm) for scale-up formulation of representative limit size nanoparticles (DSPC/Cholesterol vesicles) produced using the parallel microfluidic structure is compared to those produced using a single mixer microfluidic device in FIG. 11 (final lipid concentration was 3 mg/mL). Formulation of DSPC/Cholesterol vesicles is made using a 130 μm×300 μm mixer (channel cross-section) by mixing at a buffer:lipid-ethanol volumetric flow rate ratio of 3:1, with a total flow rate of 12 ml/min in a single microfluidic mixer. The scale-up mixer, which enables throughput of 72 ml/min (6×scaling), consists of 6 original mixers where two sets of three mixers are stacked vertically and placed next to each other horizontally. Final lipid concentration after mixing in microfluidic device is 3 mg/ml. Error bars represent standard deviation of multiple formulations made with microfluidic mixer (n=3 for 1×mixer and n=2 for 6×mixer).

Temperature-controlled Fluidic Structures. In another embodiment, the invention provides temperature-controlled fluidic structures for making limit size lipid nanoparticle. In these structures, the solution can be rapidly heated when the streams are flowed through a chamber with a high surface area (heater area) to volume ratio. COMSOL simulations showed that the solution can be heated by flowing through 10 mm×10 mm×100 um chamber at a flow rate of 1 mL/min. The simulation showed that the solution heats up in the first fifth of the chamber so the flow rate could probably increased to 5 mL/min.

Representative temperature-controlled fluidic structures are illustrated in FIGS. 12-14.

The following examples are provided for the purpose of illustrating, not limiting, the invention.

EXAMPLES

Example 1

Preparation and Characterization of Representative LNP

In this example, the preparation and characterization of representative LNP are described.

Lipids and Chemicals. 1-palmitoyl-2-oleoyl-sn-glycero-3-phosphocholine (POPC) was obtained from Avanti Polar Lipids (Alabaster, AL). 1,2,3-Tri(cis-9-octadecenoyl) glycerol (glyceryl trioleate, TO), cholesterol (Chol), sodium chloride, ammonium sulfate, and doxorubicin hydrochloride were from Sigma-Aldrich Canada Ltd. (Oakville, Ontario, Canada).

Micromixer design and fabrication. The micromixer was a chaotic mixer for continuous flow systems with the layout based on patterns of asymmetric grooves on the floor of the channel (staggered herringbone design) that induce a repeated sequence of rotational and extensional local flows thus inducing rapid mixing of the injected streams. The device was produced by soft lithography, the replica molding of microfabricated masters in elastomer. The device features a 200 µm wide and 79 µm high mixing channel with herringbone structures formed by 31 µm high and 50 µm thick features on the roof of the channel (see FIG. 1). Fluidic connections were made with ⅟₃₂" I.D., ³⁄₃₂" O.D. tubing that was attached to 21G1 needles for connection with syringes. 1 ml, 3 ml, and 5 ml syringes were generally used for inlet streams. A dual syringe pump (KD200, KD Scientific) was used to control the flow rate through the device.

LNP formation. Lipids (POPC or POPC/Chol (55/45 molar ratio) for preparations of liposomal systems, POPC/TO at different ratios for preparations of nanoemulsions were dissolved in ethanol at 10 mg/ml of total lipid. The LNP were prepared by injecting an ethanolic lipid mixture into the first inlet and an aqueous hydration solution (saline, 154 mM NaCl) into the second inlet of the mixing channel of the micromixer (see FIG. 1). The appropriate flow rate ratios (FRR, ratio of aqueous stream volumetric flow rate to ethanolic volumetric flow rate) were set by maintaining a constant flow rate in the ethanolic channel and varying the flow rates of the aqueous channel (typically 0.5-4.5 ml/min). Aqueous dispersions of LNP formed this way were collected from the outlet stream resulting from the mixing of two adjacent streams and dialyzed against 154 mM saline to remove the residual ethanol.

Formation of POPC LNP exhibiting ammonium sulfate gradient. Limit size vesicular POPC LNP containing ammonium sulfate were formed as described above except that saline was replaced with 300 mM ammonium sulfate solution (FRR 3, 10 mg/ml POPC in ethanolic solution). After formation, the LNP were dialyzed against 300 mM ammonium sulfate and concentrated to 10 mg/ml with the use of the Amicon Ultra-15 centrifugal filter units (Millipore). An ammonium sulfate gradient was generated by exchanging the extravesicular solution with 154 mM NaCl, pH 7.4 on Sephadex G-50 spin columns.

Doxorubicin loading and assay. Doxorubicin hydrochloride was dissolved in saline at 5 mg/ml and added to the ammonium sulfate-containing LNP to give molar drug-to-lipid ratios of 0.05, 0.1, and 0.2. The samples were then incubated at 60° C. for 30 min to provide optimal loading conditions. Unentrapped doxorubicin was removed by running the samples over Sephadex G-50 spin columns prior to detection of entrapped drug.

Doxorubicin was assayed by fluorescence intensity (excitation and emission wavelengths 480 and 590 nm, respectively) with a Perkin-Elmer LS50 fluorimeter (Perkin-Elmer, Norwalk, CT), the value for 100% release was obtained by addition of 10% Triton X-100 to a final concentration of 0.5%. Phospholipid concentrations were determined by an enzymatic colorimetric method employing a standard assay kit (Wako Chemicals, Richmond, VA). Loading efficiencies were determined by quantitating both drug and lipid levels before and after separation of external drug from LNP encapsulated drug by size exclusion chromatography using Sephadex G-50 spin columns and comparing the respective drug/lipid ratios.

Particle size measurement. LNP were diluted to appropriate concentration with saline and mean particle size (number-weighted) was determined by dynamic light scattering (DLS) using a NICOMP model 370 submicron particle sizer (Particle Sizing Systems, Santa Barbara, CA). The sizer was operating in the vesicle and solid particle modes to determine the size of the liposomes (POPC and POPC/Chol systems) and lipid core nanospheres (POPC/TO systems), respectively.

Nuclear magnetic resonance spectroscopy. Proton decoupled $^{31}$P-NMR spectra were obtained using a Bruker AVII 400 spectrometer operating at 162 MHz. Free induction decays (FID) corresponding to about 10,000 scans were obtained with a 15 µs, 55-degree pulse with a 1 s interpulse delay and a spectral width of 64 kHz. An exponential multiplication corresponding to 50 Hz of line broadening was applied to the FID prior to Fourier transformation. The sample temperature was regulated using a Bruker BVT 3200 temperature unit. Measurements were performed at 25° C.

Cryo-transmission electron microscopy (cryo-TEM). Samples were prepared by applying 3 µL of PBS containing LNP at 20-40 mg/ml total lipid to a standard electron microscopy grid with a perforated carbon film. Excess liquid was removed by blotting with a Vitrobot system (FEI, Hillsboro, OR) and then plunge-freezing the LNP suspension in liquid ethane to rapidly freeze the vesicles in a thin film of amorphous ice Images were taken under cryogenic conditions at a magnification of 29K with an AMT HR CCD side mount camera. Samples were loaded with a Gatan 70 degree cryo-transfer holder in an FEI G20 Lab6 200 kV TEM under low dose conditions with an underfocus of 5-8 µm to enhance image contrast.

While illustrative embodiments have been illustrated and described, it will be appreciated that various changes can be made therein without departing from the spirit and scope of the invention.

The embodiments of the invention in which an exclusive property or privilege is claimed are defined as follows:

1. A device for producing limit size lipid nanoparticles having a diameter from 10 nm to 50 nm, comprising:
   (a) a first inlet for receiving a first solution comprising a first solvent;
   (b) a first inlet microchannel in fluid communication with the first inlet to provide a first stream comprising the first solvent;
   (c) a second inlet for receiving a second solution comprising lipid particle-forming materials in a second solvent;
   (d) a second inlet microchannel in fluid communication with the second inlet to provide a second stream comprising the lipid particle-forming materials in the second solvent; and
   (e) a third microchannel for receiving the first and second streams, wherein the third microchannel has a first region adapted for flowing the first and second streams and a second region adapted for mixing the contents of the first and second streams to provide a third stream comprising limit size lipid nanoparticles, wherein the third microchannel is configured to receive the first and second streams at a flow rate ratio greater than 1.0, and wherein the second region is configured to provide a fluid flow rate from 1 ml/min to 40 ml/min.

2. The device of claim 1, wherein the second region of the third microchannel has a height of 79 microns to 130 microns.

3. The device of claim 1, wherein the second region of the third microchannel comprises a micromixer.

4. The device of claim 1, wherein the second region of the third microchannel comprises bas-relief structures.

5. The device of claim 4, wherein the bas-relief structures comprise a plurality of herringbone bas-relief structures.

6. The device of claim 1, wherein the second region of the third microchannel has a principal flow direction and one or more surfaces having at least one groove or protrusion defined therein, the at least one groove or protrusion having an orientation that forms an angle with the principal direction.

7. The device of claim 1, wherein the first inlet microchannel and the second inlet microchannel each include at least a portion that has a hydraulic diameter of 20 microns to 300 microns.

8. A method of producing limit size lipid nanoparticles having a diameter from 10 nm to 50 nm, the method comprising:

flowing a first stream through a first inlet microchannel of a fluidic device, the first stream comprising a first solvent;

flowing a second stream through a second inlet microchannel of the fluidic device to provide a second stream comprising lipid particle-forming materials in a second solvent; and flowing the first stream and the second stream through a first region of a third microchannel of the fluidic device, the third microchannel in fluidic communication with the first inlet microchannel and the second inlet microchannel, wherein a flow ratio of the first stream and the second stream is greater than 1.0;

mixing the first stream and the second stream in a second region of the third microchannel, the second region in fluidic communication with the first region, wherein a combined flow rate of the first stream and the second stream in the second region is from 1 ml/min to 40 ml/min; and flowing a third stream from the second region, the third stream comprising limit size lipid nanoparticles formed by the mixing of the first stream and the second stream.

9. The method of claim 8, wherein the second region of the third microchannel has a height of 79 microns to 130 microns.

10. The method of claim 8, wherein the second region of the third microchannel comprises a micromixer.

11. The method of claim 8, wherein the second region of the third microchannel comprises bas-relief structures.

12. The method of claim 11, wherein the bas-relief structures comprise a plurality of herringbone bas-relief structures.

13. The method of claim 8, wherein the second region of the third microchannel has a principal flow direction and one or more surfaces having at least one groove or protrusion defined therein, the at least one groove or protrusion having an orientation that forms an angle with the principal direction.

14. The method of claim 8, wherein the first inlet microchannel and the second inlet microchannel each include at least a portion that has a hydraulic diameter of 20 microns to 300 microns.

15. A system, comprising:

a first inlet microchannel configured to receive a first solution and provide a first stream comprising the first solution;

a second inlet microchannel configured to receive a second solution and provide a second stream comprising the second solution;

a third microchannel configured to receive the first stream and the second stream, wherein the third microchannel has a first region adapted for flowing the first stream and the second stream and a second region adapted for mixing the first stream and the second stream to provide a third stream comprising a mixture of the first solution and the second solution;

a first pump configured to provide the first solution to the first inlet microchannel at a first flow rate; and a second pump configured to provide the second solution to the second inlet microchannel at a second flow rate;

wherein the ratio of the first flow rate to the second flow rate is greater than 1.0, and wherein the second region is configured to provide a fluid flow rate from 1 ml/min to 40 ml/min.

16. The system of claim 15, wherein the second region of the third microchannel comprises a micromixer.

17. The system of claim 15, wherein the second region of the third microchannel comprises bas-relief structures.

18. The system of claim 15, wherein the second region of the third microchannel has a principal flow direction and one or more surfaces having at least one groove or protrusion defined therein, the at least one groove or protrusion having an orientation that forms an angle with the principal direction.

19. The system of claim 15, wherein the first inlet microchannel and the second inlet microchannel each include at least a portion that has a hydraulic diameter of 20 microns to 300 microns.

* * * * *